(12) United States Patent
Matsuura et al.

(10) Patent No.: US 12,097,177 B2
(45) Date of Patent: Sep. 24, 2024

(54) THERAPEUTIC METHOD FOR CAT WITH CHRONIC KIDNEY DISEASE

(71) Applicant: Toray Industries, Inc., Tokyo (JP)

(72) Inventors: Takumi Matsuura, Tokyo (JP);
Hajimu Kurumatani, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 18/565,161

(22) PCT Filed: Jun. 15, 2022

(86) PCT No.: PCT/JP2022/023876
§ 371 (c)(1),
(2) Date: Nov. 29, 2023

(87) PCT Pub. No.: WO2022/265031
PCT Pub. Date: Dec. 22, 2022

(65) Prior Publication Data
US 2024/0207218 A1    Jun. 27, 2024

(30) Foreign Application Priority Data
Jun. 16, 2021    (JP) .................................. 2021-100475

(51) Int. Cl.
*A61K 31/343* (2006.01)
*A61P 13/12* (2006.01)

(52) U.S. Cl.
CPC ............ *A61K 31/343* (2013.01); *A61P 13/12* (2018.01)

(58) Field of Classification Search
CPC .................................................... A61K 31/343
USPC ........................................................ 514/468
See application file for complete search history.

(56) References Cited

U.S. PATENT DOCUMENTS

| | | | |
|---|---|---|---|
| 4,474,802 A | 10/1984 | Ohno et al. | |
| 5,086,071 A | 2/1992 | Ohno et al. | |
| 6,656,502 B1 | 12/2003 | Hara et al. | |
| 9,783,518 B2 | 10/2017 | Takenaka et al. | |
| 9,913,825 B2 | 3/2018 | Takenaka et al. | |
| 2023/0022200 A1 | 1/2023 | Kurumatani et al. | |

FOREIGN PATENT DOCUMENTS

| | | |
|---|---|---|
| JP | H01-53672 B2 | 11/1989 |
| JP | H03-7275 A | 1/1991 |
| JP | H06-62599 B1 | 8/1994 |
| JP | H07-5582 B2 | 1/1995 |
| WO | 98/41210 A1 | 9/1998 |
| WO | 2004/103350 A1 | 12/2004 |
| WO | 2007/007668 A1 | 1/2007 |
| WO | 2016/031949 A1 | 3/2016 |
| WO | 2021/132302 A1 | 7/2021 |

OTHER PUBLICATIONS

Cathy E. Langston et al., "Applications and Outcome of Hemodialysis in Cats: a Review of 29 Cases," Journal of Veterinary Internal Medicine, vol. 11, No. 6 Nov.-Dec. 1997, pp. 348-355.
Masahiko Takenaka et al., "Examination of therapeutic effects of beraprost sodium on feline chronic renal failure," The 26th Annual Meeting of Japanese Society of Clinical Veterinary Medicine, 2005, pp. 72-76 (Abstract).
David J. Polzin et al. (eds.), "Chronic Kidney Disease," Textbook of Veterinary Internal Medicine, 6th, vol. 2: Chapter 260, 2005, pp. 1756-1785.
Harriet M. Syme et al., "Survival of Cats with Naturally Occurring Chronic Renal Failure Is Related to Severity of Proteinuria," J Vet Intern Med, vol. 20, No. 3, 2006, pp. 528-535.
Jonathan N. King et al., "Tolerability and Efficacy of Benazepril in Cats with Chronic Kidney Disease," J Vet Intern Med, vol. 20, No. 5, 2006, pp. 1054-1064.
Hisashi Mizutani et al., "Evaluation of the Clinical Efficacy of Benazepril in the Treatment of Chronic Renal Insufficiency in Cats," J Vet Intern Med, vol. 20, No. 5, 2006, pp. 1074-1079.
Takayuki Fujita, Vascular Biology & Medicine, vol. 7, 2006, pp. 281-290 (Abstract).

(Continued)

*Primary Examiner* — Raymond J Henley, III
(74) *Attorney, Agent, or Firm* — DLA Piper LLP (US)

(57) ABSTRACT

A therapeutic method for a cat treats chronic kidney disease to inhibit progression of chronic kidney disease into IRIS stage 4 or kidney death of a cat or improve the overall survival rate or the observed survival rate. The therapeutic method for a cat with chronic kidney disease inhibits progression of chronic kidney disease into IRIS stage 4 or kidney death of a cat by administering a therapeutic agent comprising, as an active ingredient, a compound represented by the formula (I) to a cat with stage 3 or 4 chronic kidney disease defined by the staging system established by the International Renal Interest Society (the IRIS staging) in an amount of 90 to 130 μg of the compound represented by formula (I) daily:

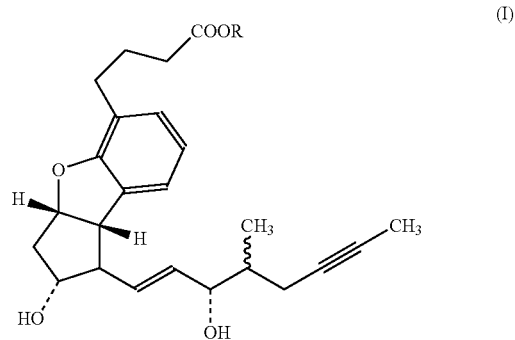

wherein R represents hydrogen or a pharmacologically acceptable cation.

55 Claims, 10 Drawing Sheets

(56) References Cited

OTHER PUBLICATIONS

Jonathan N. King et al., "Prognostic Factors in Cats with Chronic Kidney Disease," J Vet Intern Med, vol. 21, No. 5, 2007, pp. 906-916.
Toshifumi Watanabe et al., "Effects of Benazepril Hydrochloride in Cats with Experimentally Induced or Spontaneously Occurring Chronic Renal Failure," J. Vet. Med. Sci., vol. 69, No. 10, 2007, pp. 1015-1023.
L.M. Boyd et al., "Survival in Cats with Naturally Occurring Chronic Kidney Disease (2000-2002)," J Vet Intern Med, vol. 22, No. 5, 2008, pp. 1111-1117.
Leyenda Harley et al., "Proteinuriain dogs and cats," Can Vet J, vol. 53, No. 6, 2012, pp. 631-638.
S. Chakrabarti et al., "Clinicopathological Variables Predicting Progression of Azotemia in Cats with Chronic Kidney Disease," J Vet Intern Med, vol. 26, No. 2, 2012, pp. 275-281.
S. Chakrabarti et al., "Histomorphometry of Feline Chronic Kidney Disease and Correlation With Markers of Renal Dysfunction," Veterinary Pathology, vol. 50, No. 1, 2012, pp. 147-155.
Yasufumi Goto et al., "A prostacyclin analog prevents the regression of renal microvascular network by inhibiting mitochondria-dependent apoptosis in the kidney of rat progressive glomerulonephritis," Prostaglandins and Other Lipid Mediators, vol. 112, 2014, pp. 16-26.
J.L. Pouchelon et al., "Cardiovascular-renal axis disorders in the domestic dog and cat: a veterinary consensus statement," Journal of Small Animal Practice, vol. 56, No. 9, 2015, pp. 537-552.
U. Sent et al., "Comparison of Efficacy of Long-term Oral Treatment with Telmisartan and Benazepril in Cats with Chronic Kidney Disease," Journal of Veterinary Internal Medicine, vol. 29, No. 6, 2015, pp. 1479-1487.
R.F. Geddes et al., "Relationship between Plasma Fibroblast Growth Factor-23 Concentration and Survival Time in Cats with Chronic Kidney Disease," Journal of Veterinary Internal Medicine, vol. 29, No. 6, 2015, pp. 1494-1501.
S.M. McLeland et al., "A Comparison of Biochemical and Histopathologic Staging in Cats With Chronic Kidney Disease," Veterinary Pathology, vol. 52, No. 3, 2015, pp. 524-534.
Martha Cannon, "Diagnosis and investigation of chronic kidney disease in cats," In Practice, vol. 38, Oct. 2016, pp. 2-9.
Andrew H. Sparkes et al., "ISFM Consensus Guidelines on the Diagnosis and Management of Feline Chronic Kidney Disease," Journal of Feline Medicine and Surgery, vol. 18, No. 3, 2016, pp. 219-239.
L.M. Freeman et al., "Evaluation of Weight Loss Over Time in Cats with Chronic Kidney Disease," Journal of Veterinary Internal Medicine, vol. 30, No. 5, 2016, pp. 1661-1666.
C.A. Brown et al., "Chronic Kidney Disease in Aged Cats: Clinical Features, Morphology, and Proposed Pathogeneses," Veterinary Pathology, vol. 53, No. 2, 2016, pp. 309-326.
Natalie C. Finch et al., "Development of an estimated glomerular filtration rate formula in cats," Journal of Veterinary Internal Medicine, vol. 32, No. 6, 2018, pp. 1970-1976.
Yuki Hattori, "Six updated cases of treatment of feline chronic kidney disease (CKD) with beraprost sodium," Small Animal Clinic, No. 188, Oct. 2017, pp. 10-17 (Abstract).
Reeko Sato et al., "Update on treatment of feline chronic kidney disease with beraprost sodium (BPS)," J-VET, vol. 372, Mar. 2018, pp. 56-67 (Abstract).

Boehringer Ingelheim Vetmedica Inc., Freedom of Information Summary, Original New Animal Drug Application, NADA 141-501, Semintra® (telmisartan oral solution), Oral Solution Cats, for the control of systemic hypertension in cats, May 15, 2018.
M. Takenaka et al., "A Double-blind, Placebo-controlled, Multicenter, Prospective, Randomized Study of Beraprost Sodium Treatment for Cats with Chronic Kidney Disease," Journal of Veterinary Internal Medicine, vol. 32, 2018, pp. 236-248.
Takuo Ishida, "Treatment of feline chronic kidney disease with beraprost sodium-Results from prolonged treatments," $9^{th}$ WJVF Proceeding, Jul. 2018, pp. 164-165 (Abstract).
IRiS (International Renal Interest Society) Treatment Recommendations for CKD in Cats (2019), http://www.iris-kidney.com/education/staging_system.html., Accessed Mar. 2021.
IRiS (International Renal Interest Society) Staging of CKD (modified 2019), "1. Staging of CKD based on blood creatinine and SDMA concentrations," pp. 1-5.
Hiroyuki Ito, "Drug therapy for feline chronic kidney disease—ACEI, ARB, beraprost—Facts of therapeutic agents, selection, and treatment—based on actual cases," $16^{th}$ JCVIM Proceeding, vol. 2, Feb. 2019, pp. 106-107 (Abstract).
Mitsunobu Kawazu, "Report on use of therapeutic agent (RAPROS) 0n feline chronic kidney disease," Small Animal Clinic, No. 193, Feb. 2019, pp. 12-17 (Abstract).
Hiroyuki Ito, "A veterinary clinician statement of key pharmaceutical therapy for chronic kidney disease in cats: the renin-angiotensin blockers and beraprost sodium." $10^{th}$ WJVF Proceeding. Jul. 2019. pp. 275-279 (Abstract).
Megan Conroy et al., "Chronic kidney disease in cats attending primary care practice in the UK: a VetCompass™ study," Veterinary Record, 2019, pp. 1-9.
Package Insert of RAPROS™ (partial translation).
Inc. EU. Freedom of Information Summary: Original New Animal Drug Application, NADA 141-536, Elura™ capromorelin oran solution Cata, for management of weight loss in cats with chronic kidney disease, Oct. 16, 2020.
Hiroyuki Ito, "Drug therapy for feline chronic kidney disease from the viewpoint of clinical veterinarian, What is promising for improved QOL and long-term survival?" MVM, vol. 29, No. 192, 2020, pp. 101-107 (Abstract).
Yuichi Miyagawa, Kidney cycling—Use of drugs for chronic kidney disease—Stage 25, ACE inhibitor and angiotensin 2 receptor blockers, MVM, vol. 30, No. 194, Jan. 2021, pp. 95-98 (Abstract).
Yuichi Miyagawa, "Kidney cycling—Use of drugs for chronic kidney disease—Stage 26, Beraprost sodium," MVM, vol. 30, No. 195, Mar. 2021, pp. 79-83 (Abstract).
International Search Report dated Aug. 16, 2022 in counterpart International Application No. PCT/JP2022/023876 w/English translation.
Written Opinion dated Aug. 16, 2022 in counterpart International Application No. PCT/JP2022/023876.
Kazuhisa Matsumoto et al., "Pharmacokinetics and Biotransformation of Beraprost Sodium I: Plasma Level Profile of Beraprost Sodium in Rat." *Yakubutsu Dotai* (Pharmacokinetics), vol. 4, No. 6, 1989, pp. 713-725.
Masahiro Shimamura MS et al., "The Pharmacokinetics of Beraprost Sodium Following Single Oral Administration to Subjects With Impaired Kidney Function," The Journal of Clinical Pharmacology, vol. 57, Issue 4, 2017, pp. 524-535 (Abstract).
$1^{st}$ Office Action dated Apr. 11, 2023 in counterpart JP 2022-542656.
$2^{nd}$ Office Action dated May 30, 2023 in counterpart JP 2022-542656 w/English translation.
Decision to Grant a Patent dated Jun. 20, 2023 in counterpart JP 2022-542656 w/English translation.

Classification of complications and comorbidities

Fig. 4

Case summary

| Group | Stage progression | Discontinuation | Overall |
|---|---|---|---|
| BPS therapy group | 3 | 34 | 37 |
| No BPS therapy group | 15 | 317 | 332 |

3-year stage progression-free rate

| | | | 95% confidence interval | |
|---|---|---|---|---|
| Group | Stage progression-free rate | Standard Error | Lower limit | Upper limit |
| BPS therapy group | 74.7 | 12.9 | 49.4 | 99.9 |
| No BPS therapy group | 89.6 | 2.9 | 83.9 | 95.4 |

Average stage progression-free period

| | | | 95% confidence interval | |
|---|---|---|---|---|
| Group | Mean | Standard Error | Lower limit | Upper limit |
| BPS therapy group | 38.0 | 2.1 | 33.9 | 42.1 |
| No BPS therapy group | 40.9 | 0.5 | 39.9 | 42.0 |

Fig. 6

Case summary

| Group | Kidney death | Discontinuation | Overall |
|---|---|---|---|
| BPS therapy group | 1 | 36 | 37 |
| No BPS therapy group | 8 | 324 | 332 |

3-year kidney survival rate

| | | | 95% confidence interval | |
|---|---|---|---|---|
| Group | Kidney survival rate | Standard Error | Lower limit | Upper limit |
| BPS therapy group | 90.0 | 9.5 | 71.4 | 100.0 |
| No BPS therapy group | 95.2 | 1.9 | 91.5 | 98.9 |

Average period before kidney death

| | | | 95% confidence interval | |
|---|---|---|---|---|
| Group | Mean | Standard Error | Lower limit | Upper limit |
| BPS therapy group | 40.8 | 1.3 | 38.3 | 43.3 |
| No BPS therapy group | 41.9 | 0.4 | 41.1 | 42.7 |

Fig. 9

Case summary

| Group | Death | Discontinuation | Overall |
|---|---|---|---|
| BPS therapy group | 10 | 27 | 37 |
| No BPS therapy group | 63 | 269 | 332 |

3-year overall survival rate

| | | | 95% confidence interval | |
|---|---|---|---|---|
| Group | Survival rate | Standard Error | Lower limit | Upper limit |
| BPS therapy group | 52.2 | 11.8 | 29.1 | 75.3 |
| No BPS therapy group | 72.4 | 3.3 | 65.8 | 78.9 |

Average survival period

| | | | 95% confidence interval | |
|---|---|---|---|---|
| Group | Mean | Standard Error | Lower limit | Upper limit |
| BPS therapy group | 31.5 | 2.6 | 26.3 | 36.7 |
| No BPS therapy group | 35.1 | 0.9 | 33.4 | 36.9 |

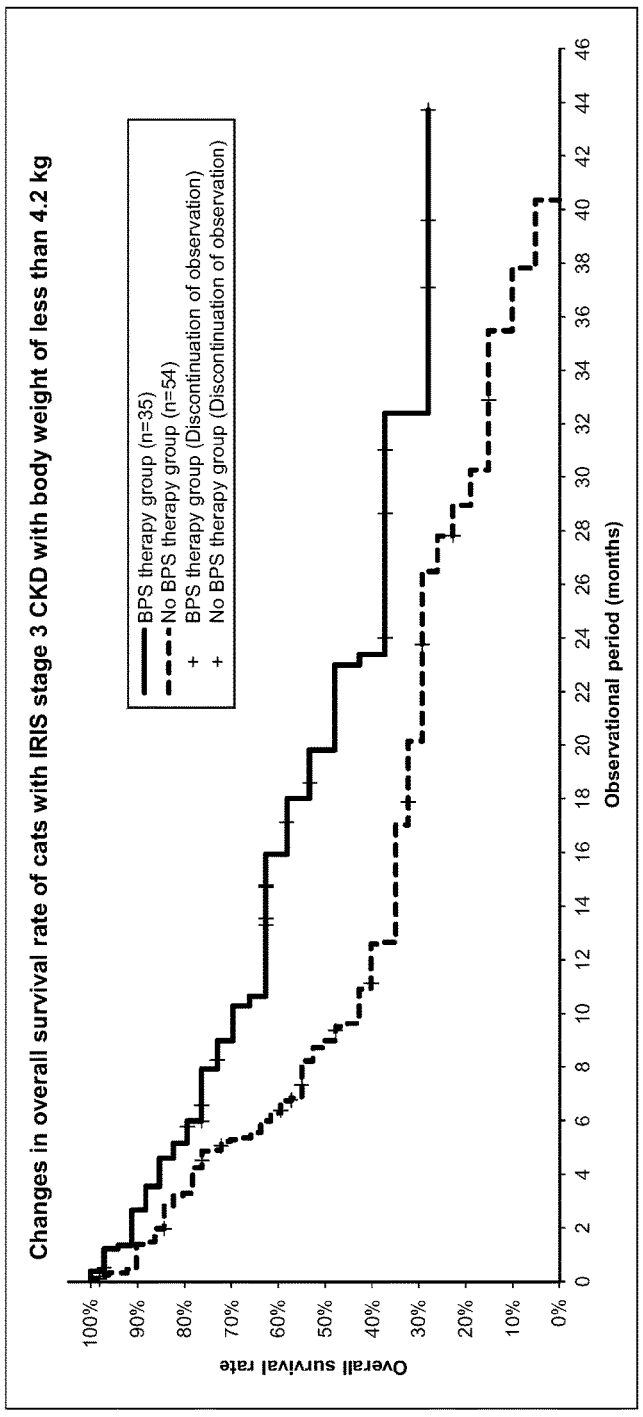

THERAPEUTIC METHOD FOR CAT WITH CHRONIC KIDNEY DISEASE

TECHNICAL FIELD

This disclosure relates to a therapeutic method for a cat with chronic kidney disease that inhibits progression into IRIS stage 4 or kidney death of a cat with chronic kidney disease or improves the overall survival rate or observed survival rate.

BACKGROUND

Chronic kidney disease ("CKD") in cats is the leading cause of death in 5-year-old or older cats, the prevalence rate of CKD rises with age, which is as high as approximately 30% to 40% at the age of 10 or older (Sparkes A H, Caney S, Chalhoub S, et al., ISFM Consensus Guidelines on the Diagnosis and Management of Feline Chronic Kidney Disease, J. Feline Med. Surg., 2016; 18(3): 219-239), and CKD is the critical health problem for companion animals.

Feline CKD is a pathological condition under which kidney dysfunctions progress over time, and its end-stage is an end-stage CKD characterized by an irreversible structural lesion of the kidney. The end-stage CKD can be treated by kidney transplantation and hemodialysis (Polzin O, Ross. Ettinger S J, Feldman C E (eds.), Textbook of Veterinary Internal Medicine, 6$^{th}$, 2005; Vol. 2: Chapter 260, 1756-1785). However, treatment by kidney transplantation is a less-advanced method because there is no organization such as a kidney bank for human patients and it is difficult to acquire donor animals. Also, application of hemodialysis to feline chronic renal failure is very limited because of a technically complicated procedure, a high treatment cost, and chronic debilitation (Langston C E, Cowgill L D, Spano J A., Applications and outcome of hemodialysis in cats: a review of 29 case, J. Vet. Intern. Med., 1997; 11(6): 348-355). Since treatment options for the end-stage feline CKD are limited, a novel method of treatment that can surely delay clinical stage progression and improve the survival rate has been awaited.

Feline CKD is known to involve impaired kidney function and impaired cardiovascular functions and it is referred to as "cardiovascular-renal axis disorders" (Pouchelon J L, Atkins C E, Bussadori C, et al., Cardiovascular-renal axis disorders in the domestic dog and cat: a veterinary consensus statement, J. Small Anim. Pract., 2015; 56(9): 537-552). Accordingly, many cats with CKD die of heart failure instead of CKD. In addition, the International Society of Feline Medicine provides, in the guidelines on treatment and management of feline CKD, examples of complications/comorbidities associated with worsening of feline CKD such as hypertension, proteinuria, hypokalemia, hyperphosphatemia, urinary tract infection, anemia, and CKD-mineral bone disorder (A. H. Sparkes et al.), and such complications/comorbidities are known to cause death because of feline CKD. Accordingly, the most important indicator for evaluation of treatment methods for feline CKD can be the overall survival rate or observed survival rate that encompasses all death caused by other factors such as the complications/comorbidities mentioned above, in addition to death because of CKD.

While the guidelines from the International Society of Feline Medicine exemplify, as therapeutic agents for feline CKD, phosphate binders, active vitamin D3 analogs, calcium channel blockers, B blockers, erythrocyte-stimulating agents, angiotensin-converting enzyme inhibitors, angiotensin receptor blockers, nurokinin-1 receptor antagonists, nonadrenergic and specific serotonergic antidepressants, 5-hydroxytryptamine receptor 4 agonists, 5-hydroxytryptamine receptor 3 antagonists, histamine-2 receptor blockers, and proton pump inhibitors, effects of such agents to improve the International Renal Interest Society (hereafter, abbreviated to as "IRIS") stage, the overall survival rate, or the observed survival rate of feline CKD are not demonstrated at all (A. H. Sparkes et al.).

IRIS has proposed the clinical stratification consisting of diagnosis of feline CKD and staging shown in Table 1 below ("the IRIS staging") (International Renal Interest Society, IRIS Treatment Recommendations for CKD, http://www.iris-kidney.com/education/staging_system.html., Accessed March 2021) and the IRIS staging has been extensively approved internationally (Cannon M, Diagnosis and investigation of chronic kidney disease in cats, In Practice, 2016; 38: 2-9). The IRIS staging enables diagnosis of feline CKD as described below. Specifically, patient animals are diagnosed to have feline CKD when at least one of the following indicators is persistently observed on the basis of the medical history and the results of physical examination, clinical examination, diagnostic imaging, and histopathological examination of patient animals in stable condition. That is, elevated serum creatinine or serum symmetric dimethylarginine ("SDMA"), persistent elevation in serum SDMA to higher than 14 μg/dL, renal proteinuria accompanied by the persistent urine protein:creatinine (UPC) ratio of higher than 0.4, the urine specific gravity of lower than 1.035, inappropriate tubular loss of potassium, bicarbonate, glucose or amino acid, renal cyst, urolith, and renal tumor. Subsequently, the IRIS staging can be performed as described below on the basis of assessment of serum creatinine or serum SDMA or preferably serum creatinine and serum SDMA via two or more hospital visits: stage 1: serum creatinine of lower than 1.6 mg/dL or serum SDMA of lower than 18 μg/dL or preferably serum creatinine of lower than 1.6 mg/dL and serum SDMA of lower than 18 μg/dL; stage 2: serum creatinine of 1.6 to 2.8 mg/dL or serum SDMA of 18 to 25 μg/dL or preferably serum creatinine of 1.6 to 2.8 mg/dL and serum SDMA of 18 to 25 μg/dL; stage 3: serum creatinine of 2.9 to 5.0 mg/dL or serum SDMA of 26 to 38 μg/dL or preferably serum creatinine of 2.9 to 5.0 mg/dL and serum SDMA of 26 to 38 μg/dL; and stage 4: serum creatinine of higher than 5.0 mg/dL or serum SDMA of higher than 38 μg/dL or preferably serum creatinine of higher than 5.0 mg/dL and serum SDMA of higher than 38 μg/dL (International Renal Interest Society, IRIS Treatment Recommendations for CKD). As described above, the IRIS staging is considered to play a key role as an indicator in evaluation of severity of feline CKD, which is different from serum creatinine as the indicator by itself.

TABLE 1

IRIS staging Step 1: Diagnosis of feline CKD

* Based on medical history and results of physical examination, clinical examination, diagnostic imaging, and histopathological examination
* At least one of the following criteria is persistently observed

| Criteria |
| --- |
| (1) Decreased glomerular filtration rate<br>Azotemia is observed: elevated serum creatinine or serum SDMA;<br>persistent elevation in serum SDMA to >14 μg/dL<br>(2) Loss of normal glomerular function |

TABLE 1-continued

Renal proteinuria is observed: persistent UPC ratio of >0.4
(3) Loss of normal tubular function
Inappropriate urine specific gravity is observed: urine specific gravity of <1.035
In addition, inappropriate tubular loss of potassium, bicarbonate, glucose or amino acid: based on the results of clinical examination
(4) Abnormalities in renal structure
Renal cyst, urolith, and renal tumor are observed: based on the results of diagnostic imaging or histopathological examination IRIS staging Step 2: Staging of feline CKD

| Evaluation criteria | Stage 1 | Stage 2 | Stage 3 | Stage 4 |
|---|---|---|---|---|
| Serum creatinine (mg/dL) | <1.6 | 1.6-2.8 | 2.9-5.0 | >5.0 |
| Serum SDMA (μg/dL) | <18 | 18-25 | 26-38 | >38 |
| UPC ratio Substaging | Nonproteinuric: <0.2; borderline proteinuric: 0.2-0.4; proteinuric: >0.4 | | | |
| Maximal blood pressure (mmHg) Substaging | Normotensive: <140; prehypertensive: 140-159; hypertensive: 160-179; severely hypertensive: ≥180 | | | |

The International Society of Feline Medicine proposes, in the guidelines on treatment and management of feline CKD, that the IRIS staging is associated with the survival rate of cats with CKD and that serum creatinine by itself is insufficient as the indicator for kidney function evaluation (A. H. Sparkes et al.,). While a formula to calculate a kidney function indicator of feline CKD similar to the estimated glomerular filtration rate for human patients based on serum creatinine had been studied, such study was reported to end up in failure (Finch N C, Syme H M, Elliott J, Development of an estimated glomerular filtration rate formula in cats, J. Vet. Intern. Med., 2018; 32(6): 1970-1976). Accordingly, it is considered necessary to predict the survival rate of feline CKD based on the IRIS staging, and it is considered difficult to predict such survival rate based only on serum creatinine.

In feline CKD, the prevalence rate of proteinuria is reported to be 16% (Geddes R F, Elliott J, Syme H M, Relationship between plasma fibroblast growth factor-23 concentration and survival time in cats with chronic kidney disease, J. Vet. Intern. Med., 2015; 29(6): 1494-1501) and severity thereof is known to be associated with the lowered survival rate (Syme H M, Markwell P J, Pfeiffer D, Elliott J, Survival of cats with naturally occurring chronic renal failure is related to severity of proteinuria, J. Vet. Intern. Med., 2006; 20(3): 528-535 and King J N, Tasker S, Gunn-Moore D A, Strehlau G, Group B S, Prognostic factors in cats with chronic kidney disease, J. Vet. Intern. Med., 2007; 21(5): 906-916). As therapeutic agents of proteinuria, benazepril hydrochloride, which is an angiotensin-converting enzyme inhibitor, and telmisartan, which is an angiotensin receptor blocker, are used. Benazepril hydrochloride has been studied in terms of its clinical efficacy on feline CKD, it is reported to lower the severity of proteinuria (Mizutani H, Koyama H, Watanabe T, et al., Evaluation of the clinical efficacy of benazepril in the treatment of chronic renal insufficiency in cats, J. Vet. Intern. Med., 2006; 20(5): 1074-1079 and King J N, Gunn-Moore D A, Tasker S, Gleadhill A, Strehlau G, Benazepril in Renal Insufficiency in Cats Study G, Tolerability and efficacy of benazepril in cats with chronic kidney disease, J. Vet. Intern. Med., 2006; 20(5): 1054-1064), and it is reported to inhibit elevation in serum creatinine, which serves as an indicator of renal filtration function (Watanabe T, Mishina M, Effects of benazepril hydrochloride in cats with experimentally induced or spontaneously occurring chronic renal failure, J. Vet. Med. Sci., 2007; 69(10): 1015-1023). However, benazepril hydrochloride has not been found to inhibit progression of feline CKD stage, and its influence on the overall survival rate or the observed survival rate has not been reported (H. Mizutani et al. and J. N. King et al.). In addition, telmisartan has been also reported to improve proteinuria of feline CKD; however, improvement in the IRIS stage progression or the overall survival rate or the observed survival rate has not been studied (Sent U, Gossl R, Elliott J, Syme H M, Simmering T, Comparison of Efficacy of Long-term Oral Treatment with Telmisartan and Benazepril in Cats with Chronic Kidney Disease, J. Vet. Intern. Med., 2015; 29(6): 1479-1487 and Inc. BIV. FREEDOM OF INFORMATION SUMMARY ORIGINAL NEW ANIMAL DRUG APPLICATION NADA 141-501 Semintra™ (telmisartan oral solution) Oral Solution Cats For the control of systemic hypertension in cats, May 15, 2018). In feline CKD, the prevalence rate of body weight loss is reported to be 42% to 82% (Freeman L M, Lachaud M P, Matthews S, Rhodes L, Zollers B, Evaluation of Weight Loss Over Time in Cats with Chronic Kidney Disease, J. Vet. Intern. Med., 2016; 30(5): 1661-1666) and it is known to be associated with the lowered survival rate (Boyd L M, Langston C, Thompson K, Zivin K, Imanishi M, Survival in cats with naturally occurring chronic kidney disease (2000-2002), J. Vet. Intern. Med., 2008; 22(5): 1111-1117). As a therapeutic agent for body weight loss, a ghrelin receptor agonist, capromorelin, has been used. The clinical efficacy thereof on feline CKD has been studied, and capromorelin is reported to inhibit body weight loss. However, no improvement in the overall survival rate or the observed survival rate of feline CKD has been demonstrated (Inc. EU. FREEDOM OF INFORMATION SUMMARY ORIGINAL NEW ANIMAL DRUG APPLICATION NADA 141-536 Elura™ capromorelin oral solution Cats For management of weight loss in cats with chronic kidney disease, Oct. 16, 2020). As described above, therapeutic agents that have been reported to exert effects of improving or inhibiting worsening in poor prognostic factors of feline CKD; i.e., urine protein, serum creatinine, and body weight loss, are not approved to show improvement in IRIS stage progression and the overall survival rate or the observed survival rate.

It has been reported that 19% of cats with the feline IRIS stage 2 CKD die without stage progression and that 27% of cats with the feline IRIS stage 3 CKD die without stage progression (Chakrabarti S, Syme H M, Elliott J, Clinicopathological variables predicting progression of azotemia in cats with chronic kidney disease, J. Vet. Intern. Med., 2012; 26(2): 275-281). It is thus deduced that the survival rate is associated with factors other than a change in the IRIS stage.

Beraprost sodium ("BPS") is a prostacyclin (sometimes "PGI$_2$") derivative, and a therapeutic agent for ameliorating uremia in feline chronic renal failure comprising, as an active ingredient, BPS has been reported (WO 2007/007668). WO '668 reports that administration of BPS to a cat with uremia caused by chronic renal failure improved uremia and that recovery from chronic renal failure was observed in 2 cats with mild chronic renal failure exhibiting serum creatinine of 1.4 mg/dL to 2.0 mg/dL through administration of BPS at a dose of 150 μg twice daily for 6 months; that is, clinical symptoms of uremia was improved, serum creatinine and BUN were lowered to normal levels, and the normal state continued for a long period of time. However, A. H. Sparkes et al. thereafter reports that only serum creatinine and the like used as the indicators of the improving effects in WO '668 are insufficient as the kidney function indicators (A. H. Sparkes et al.), and it is considered impossible to predict the survival rate of feline CKD based on the creatinine level and the like. In WO '668, in addition, the survival period is not analyzed and the overall survival rate or the observed survival rate is not calculated. Further, a control group is not provided, and it is thus impossible to evaluate the survival period. Furthermore, the IRIS stage is not evaluated, and the stage progression-free rate is not calculated. That is, WO '668 does not describe or indicate inhibition of IRIS stage progression.

Examination of therapeutic effects of beraprost sodium on feline chronic renal failure; Masahiko Takenaka, Kazuaki Takashima, Hajimu Kurumatani, Nobutaka Ida, Yoshihisa Yamane, the 26$^{th}$ Annual Meeting of Japanese Society of Clinical Veterinary Medicine, 2005, 72-76 reports that administration of BPS to a cat with CKD at a dose of 150 µg twice daily for 6 months led to an improvement in kidney function evaluated with the use of serum creatinine, BUN, and other indicators and an improvement in clinical symptoms. In "Examination of therapeutic effects of beraprost sodium on feline chronic renal failure," however, the survival period is not analyzed and the overall survival rate or the observed survival rate is not calculated. Further, a control group is not provided, and it is thus impossible to evaluate the survival period. Furthermore, the IRIS stage is not evaluated, and the stage progression-free rate is not calculated. That is, "Examination of therapeutic effects of beraprost sodium on feline chronic renal failure" does not describe or indicate inhibition of IRIS stage progression.

Thereafter, BPS drugs for veterinary use were developed and clinical trials targeting cats with naturally occurring CKD that were raised by owners were performed. The trials were performed by administering BPS to cats with CKD at a dose of 55 µg twice daily for 6 months to evaluate clinical efficacy and safety of BPS as a method for treatment of cats with CKD and comparing the results with the results attained by placebo administration. Efficacy was evaluated with the use of serum creatinine, the serum phosphorus-calcium ratio, or the urine specific gravity as the major end points. Thirty one cats subjected to evaluation of efficacy to which BPS had been administered had the CKD with serum creatinine of 1.6 mg/dL to 4.1 mg/dL when the trials were initiated. For feline CKD, BPS therapy is demonstrated to be well-tolerated and safe and have inhibited serum creatinine elevation observed in the placebo group (A Double-blind, Placebo-controlled, Multicenter, Prospective, Randomized Study of Beraprost Sodium Treatment for Cats with Chronic Kidney Disease, M. Takenaka, J. Vet. Intern. Med., 2018; 32: 236-248). In "A Double-blind, Placebo-controlled, Multicenter, Prospective, Randomized Study of Beraprost Sodium Treatment for Cats with Chronic Kidney Disease," however, the survival period is not analyzed and the overall survival rate or the observed survival rate is not calculated. Further, the IRIS stage is not evaluated, and the stage progression-free rate is not calculated. That is, "A Double-blind, Placebo-controlled, Multicenter, Prospective, Randomized Study of Beraprost Sodium Treatment for Cats with Chronic Kidney Disease" does not describe or indicate inhibition of IRIS stage progression.

A therapeutic agent for feline chronic renal failure comprising, as an active ingredient, BPS for which the above-described trials are described as the examples has been reported (WO 2016/031949). WO '949 reports that administration of BPS at a dose of 55 µg or continuous administration of BPS at a dose of 6 to 26.4 µg/kg, preferably twice daily for 30 days or longer, to cats with chronic renal failure can inhibit elevation in kidney function marker values such as serum creatinine and BUN, and stabilize the conditions without adverse side effects. In WO '949, however, the survival period is not analyzed and the overall survival rate or the observed survival rate is not calculated. Further, the IRIS stage is not evaluated, and the stage progression-free rate is not calculated. That is, WO '949 does not describe or indicate inhibition of IRIS stage progression.

Based on the results of the test, manufacture and marketing of the BPS drugs for veterinary use were approved in Japan to inhibit impairment in kidney function and improve clinical symptoms of the feline IRIS stages 2 to 3 CKD and such BPS drugs have been used in clinical settings as RAPROS (trademark) (Toray Industries, Inc.). The usage thereof is oral administration of a tablet of RAPROS comprising, as an active ingredient, 55 µg of BPS twice daily after morning and evening feeding occasions.

Several other treatment outcomes and results of observation studies using RAPROS (trademark) are reported.

Six updated cases of treatment of feline chronic kidney disease (CKD) with beraprost sodium, Yuki Hattori S A C, No. 188, 2017 (October), 10-17 reports treatment outcomes of administration of BPS at a dose of 20 to 55 µg twice daily to cats with CKD. When BPS administration was initiated, six subject cats exhibited serum creatinine of 2.0 mg/dL to 4.4 mg/dL, BPS was administered at a dose of 20 to 55 µg twice daily, and the administration period was for 2 months to 3 years and 3 months. "Six updated cases of treatment of feline chronic kidney disease (CKD) with beraprost sodium" demonstrates changes in serum creatinine of all the cases and SDMA of some of the cases during the observational period, and "Six updated cases of treatment of feline chronic kidney disease (CKD) with beraprost sodium" describes that use of BPS leads to stabilized clinical symptoms and maintained kidney function. In "Six updated cases of treatment of feline chronic kidney disease (CKD) with beraprost sodium," however, the survival period is not analyzed and the overall survival rate or the observed survival rate is not calculated. Further, a control group is not provided, and it is thus impossible to evaluate the survival period. Furthermore, the IRIS stage is not evaluated, and the stage progression-free rate is not calculated. That is, "Six updated cases of treatment of feline chronic kidney disease (CKD) with beraprost sodium" does not describe or indicate inhibition of IRIS stage progression.

Finding through beraprost sodium (BPS) treatment-continuous treatment of feline chronic kidney disease (CKD), Takuo Ishida, the 9$^{th}$ WJVF Proceeding, 2018 (July), 164-165 reports treatment outcomes of administration of BPS at a dose of 55 µg twice daily for 3 to 13 months to cats with CKD examined at 14 animal hospitals. When BPS administration was initiated, 14 subject cats exhibited serum creatinine of 2.3 mg/dL to 12.1 mg/dL. "Finding through beraprost sodium (BPS) treatment-continuous treatment of feline chronic kidney disease (CKD)" demonstrates, as treatment outcomes, changes in serum creatinine of all the cases, in SDMA of some cases, and in IRIS stages (cases 7 to 12) during the observational period. In "Finding through beraprost sodium (BPS) treatment-continuous treatment of feline chronic kidney disease (CKD)," however, the survival period is not analyzed and the overall survival rate or the observed survival rate is not calculated. Further, a control group is not provided, and it is thus impossible to evaluate the survival period. Furthermore, evaluation of the IRIS stage is limited to some of the cases, the stage progression-free rate is not calculated, and a control group is not provided. Thus, it is impossible to evaluate the period before stage progression. That is, "Finding through beraprost sodium (BPS) treatment-continuous treatment of feline chronic kidney disease (CKD)" does not describe or indicate the effects of inhibiting IRIS stage progression.

"Report on use of therapeutic agent (RAPROS) on feline chronic kidney disease," Mitsunobu Kawazu, SAC, 2019 (February), No. 193, 12-17 reports treatment outcomes of administration of BPS at a dose of 55 μg twice daily for up to 1 year and 5 months to cats with CKD. When BPS administration was initiated, 5 subject cats had the IRIS stage 2 or 3 CKD. "Report on use of therapeutic agent (RAPROS) on feline chronic kidney disease" demonstrates changes in serum creatinine, BUN, phosphorus, and body weight of all the cases during the observational period. In "Report on use of therapeutic agent (RAPROS) on feline chronic kidney disease," however, the survival period is not analyzed and the overall survival rate or the observed survival rate is not calculated. Further, a control group is not provided, and it is thus impossible to evaluate the survival period. Furthermore, the IRIS stage is not evaluated, and the stage progression-free rate is not calculated. That is, "Report on use of therapeutic agent (RAPROS) on feline chronic kidney disease" does not describe or indicate inhibition of IRIS stage progression.

"Update on treatment of feline chronic kidney disease with beraprost sodium (BPS)," Reeko Sato, Kazuaki Takashima, Masahiko Takenaka, J-VET, 2018 (March), 372, 56-67" reports treatment outcomes of administration of BPS at a dose of 55 μg twice daily to cats with CKD examined at 2 animal hospitals. When BPS administration was initiated, six subject cats at the first hospital had the IRIS stage 2 or 3 CKD. The BPS administration period was for 6 months. "Update on treatment of feline chronic kidney disease with beraprost sodium (BPS)" demonstrates, as treatment outcomes, serum creatinine, BUN, phosphorus, calcium, body weight, and clinical activity scores concerning appetite, activity score, and dehydration of all the cases during the observational period. When BPS administration was initiated, 8 subject cats at the second hospital had the IRIS stage 2 or 3 CKD. The BPS administration period was for up to 5 months. "Update on treatment of feline chronic kidney disease with beraprost sodium (BPS)" demonstrates, as treatment outcomes, serum creatinine, BUN, phosphorus, and body weight of all the cases during the observational period. In "Update on treatment of feline chronic kidney disease with beraprost sodium (BPS)," however, the survival period is not analyzed and the overall survival rate or the observed survival rate is not calculated. Further, a control group is not provided, and it is thus impossible to evaluate the survival period. Furthermore, the IRIS stage is not evaluated, and the stage progression-free rate is not calculated. That is, "Update on treatment of feline chronic kidney disease with beraprost sodium (BPS)" does not describe or indicate inhibition of IRIS stage progression.

"Drug therapy for feline chronic kidney disease from the viewpoint of clinical veterinarian, with a focus on RA system inhibitor and beraprost sodium," Hiroyuki Ito, the 10$^{th}$ WJVF Proceeding, 2019 (July), 275-279 reports the results of observation studies performed to compare the clinical effects of the renin-angiotensin system inhibitors and BPS on feline CKD. Among 288 cats that were diagnosed to have CKD and found to be in need of therapeutic intervention, subject cats were 26 cats that would fit the specified criteria. Based on the drug prescription records, 26 subject cats were divided into a renin-angiotensin system inhibitor group consisting of 15 cats and a BPS group consisting of 11 cats. The baseline characteristics were analyzed and the survival period and changes in body weight were compared and analyzed retrospectively. The cases of the BPS group subjected to administration of the both drugs were excluded. To the cats in the BPS group, BPS had been continuously administered at a dose of 55 μg twice daily for at least 5 months during the observational period. Based on the medical records, evaluation was performed by recording the dates of death and body weights of the renin-angiotensin system inhibitor group and the BPS group and comparing between groups by Kaplan-Meier analysis by designating the death and 10% body weight loss as the outcomes. The 11 subject cats subjected to evaluation upon BPS administration had CKD with serum creatinine of 2.5 mg/dL to 4.9 mg/dL when observation was initiated. The BPS administration period was for 6 months to 2 years. No differences were observed in terms of baseline characteristics between groups. In the BPS group, effects of improving the survival rate and lowering the risk of 10% body weight loss were found to be higher than those in the renin-angiotensin system inhibitor group. "Drug therapy for feline chronic kidney disease—ACEI, ARB, beraprost—Facts of therapeutic agents, selection, and treatment—Based on actual cases, Hiroyuki Ito, the 16$^{th}$ JCVIM Proceeding, 2019 (February), Vol. 2, 106-107 and "Drug therapy for feline chronic kidney disease from the viewpoint of clinical veterinarian, What is promising for improved QOL and long-term survival?, Hiroyuki Ito, MVM, Vol. 29, No. 192, 2020" published following "Drug therapy for feline chronic kidney disease from the viewpoint of clinical veterinarian, with a focus on RA system inhibitor and beraprost sodium" report the results of observation studies performed to compare the clinical effects of the renin-angiotensin system inhibitors and BPS on feline CKD by the study design similar to the observation studies performed by the author of "Drug therapy for feline chronic kidney disease from the viewpoint of clinical veterinarian, with a focus on RA system inhibitor and beraprost sodium." The observation studies do not include the cases using the both drugs in combination. Among 549 cats that were diagnosed to have CKD and found to be in need of therapeutic intervention, subject cats were 29 cats that would fit the specified criteria. Based on the drug prescription records, 29 subject cats were divided into a renin-angiotensin system inhibitor group consisting of 14 cats and a BPS group consisting of 15 cats. The baseline characteristics were analyzed and the survival period and changes in body weight were compared and analyzed retrospectively. To the cats in the BPS group, BPS had been continuously administered at a dose of 55 μg twice daily for at least 5 months during the observational period. Based on the medical records, evaluation was performed by recording the dates of death and body weights of the renin-angiotensin system inhibitor group and the BPS group and comparing between groups by Kaplan-Meier analysis by designating the death and 10% body weight loss as the outcomes. The 15 subject cats subjected to evaluation upon BPS administration had CKD with serum creatinine levels as follows: the mean: 3.1 mg/dL; the mean–the standard deviation: 2.4 mg/dL; and the mean+the standard deviation: 3.8 mg/dL, when observation was initiated. The maximal BPS administration period was for 2 years and 6 months. The baseline characteristics were very similar to each other between groups. In comparison with the renin-angiotensin system inhibitor group, no effects of improving the survival rate were observed but the effects of lowering the risk of 10% body weight loss were observed in the BPS group, unlike the case of "Drug therapy for feline chronic kidney disease from the viewpoint of clinical veterinarian, with a focus on RA system inhibitor and beraprost sodium."

"Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?," do not demonstrate the effects of BPS administration to improve the overall survival rate or the observed survival rate of cats with CKD or inhibit progression into IRIS stage 4 for the following reasons. In the aforementioned literatures, specifically, while the survival period is analyzed, the cases with complications/comorbidities are excluded from the study targets and the overall survival rate is not calculated. Further, use of the renin-angiotensin system inhibitors for cats with CKD without proteinuria or hypertension is not recommended in the guidelines on treatment and management of feline CKD from IRIS or the International Society of Feline Medicine (A. H. Sparkes et al. and "International Renal Interest Society, IRIS Treatment Recommendations for CKD"). In Japan, it is reported that the renin-angiotensin system inhibitors may rather impair kidney function when the circulating blood volume is lowered in cats with CKD due to dehydration, heart failure, or other reasons and that use thereof should be limited to the case with proteinuria and hypertension ("Kidney cycling—Use of drugs for chronic kidney disease—Stage 25, ACE inhibitor and angiotensin 2 receptor blockers," Yuichi Miyagawa, MVM, Vol. 30, No. 194, 2021 1). However, the "Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?," demonstrate that the renin-angiotensin system inhibitors outside the recommendations had been administered to 85% or more cats without proteinuria or hypertension among the cats of the renin-angiotensin system inhibitor group. In such studies, it is considered necessary to perform evaluation of BPS efficacy by taking the influence of non-recommended use of the renin-angiotensin system inhibitors into consideration. After publication of "Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?," in fact, a nephrology expert points out as follows. When kidney function mainly focused on changes in serum creatinine is employed as the indicator instead of the effects of inhibiting proteinuria, for which the renin-angiotensin system inhibitors are intended to be used, the renin-angiotensin system inhibitors would rather impair kidney function. When comparing the renin-angiotensin system inhibitors and BPS, accordingly, BPS efficacy is observed to be higher relative to the renin-angiotensin system inhibitors ("Kidney cycling—Use of drugs for chronic kidney disease—Stage 26, Beraprost sodium," Yuichi Miyagawa, MVM, Vol. 30, No. 195, 2021 3). On the basis of the findings reported in "Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?," as described above, efficacy of BPS administration on feline CKD should not be predicted. In "Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?," in addition, the IRIS stage is not evaluated, and the stage progression-free rate is not calculated. That is, "Drug therapy for feline chronic kidney disease from the viewpoint of clinical veterinarian, with a focus on RA system inhibitor and beraprost sodium," "Drug therapy for feline chronic kidney disease—ACEI, ARB, beraprost—Facts of therapeutic agents, selection, and treatment—Based on actual cases," and "Drug therapy for feline chronic kidney disease from the viewpoint of clinical veterinarian, What is promising for improved QOL and long-term survival?" do not describe or indicate inhibition of IRIS stage progression.

As described above, whether or not IRIS stage progression would be inhibited or the overall survival rate or the observed survival rate of cats with CKD would be improved by BPS administration was not described or indicated in conventional findings.

Also, therapeutic agents that are reported to have effects of improving or inhibiting worsening of poor prognostic factors such as proteinuria, elevated serum creatinine, and body weight loss, of feline CKD are reported to have no effects on IRIS stage progression, and such therapeutic agents are not demonstrated to improve the overall survival rate or the observed survival rate (H. Mizutani et al., J. N. King et al. and Inc. EU. FREEDOM OF INFORMATION SUMMARY ORIGINAL NEW ANIMAL DRUG APPLICATION NADA 141-536 Elura™ capromorelin oral solution Cats For management of weight loss in cats with chronic kidney disease). Even if effects of BPS administration on inhibition of impairment in kidney function and improvement in clinical symptoms of feline CKD are reported, accordingly, it is impossible to predict the possibility of inhibiting IRIS stage progression or improving the overall survival rate or the observed survival rate.

It is also known that, as the IRIS stage progresses into the next stage, the disease conditions of feline CKD are rapidly worsened and the survival rate is lowered (A. H. Sparkes et al., J. N. King et al. and L. M. Boyd et al.). L. M. Boyd et al. reports that the median survival period of cats with the CKD is for 1,151 days at IRIS stage 2, 778 days at IRIS stage 3, and 103 days at IRIS stage 4.

As the IRIS stage progresses, further, pathological changes such as tubular atrophy and tubulointerstitial inflammation/fibrosis, are known to become more severe in feline kidney tissue (Chakrabarti S, Syme H, Brown C, Elliott J, Histomorphometry of feline chronic kidney disease and correlation with markers of renal dysfunction, Veterinary pathology, 2013; 50(1): 147-155 and McLeland S, Cianciolo R E, Duncan C, Quimby J, A comparison of biochemical and histopathologic staging in cats with chronic kidney disease, Veterinary pathology, 2015; 52(3): 524-

534). In the kidney of a cat with CKD, chronic hypoxia induced by loss of peritubular capillaries stimulates interstitial fibrosis through upregulation of profibrotic factors and worsens inflammation. In addition, there is a report that negative feedback occurs when interstitial fibrosis causes the renal tubules to be separated from the peritubular capillaries and tubular hypoxia occurring as a consequence increases fibrosis (Brown C A, Elliott J, Schmiedt C W, Brown S A, Chronic Kidney Disease in Aged Cats: Clinical Features, Morphology, and Proposed Pathogeneses, Vet. Pathol., 2016; 53(2): 309-326). Further, Goto Y, Yamaguchi S, Tamura M, et al., A prostacyclin analog prevents the regression of renal microvascular network by inhibiting mitochondria-dependent apoptosis in the kidney of rat progressive glomerulonephritis, Prostaglandins Other Lipid Mediat., 2014; 112: 16-26 reports that BPS has pharmacological activity of improving microvascular network failure of kidney tissue. Based thereon, effects of BPS on feline CKD had heretofore been deduced to be high on feline CKD at an earlier stage where pathological changes in kidney tissue such as tubular atrophy or tubulointerstitial inflammation/fibrosis, are mild.

"Examination of therapeutic effects of beraprost sodium on feline chronic renal failure" reports treatment outcomes of administration of BPS at a dose of 150 µg twice daily for 6 months to 12 cats with mild, moderate, and severe CKD. The subject cats were 4 cats exhibiting serum creatinine of 1.6 mg/dL to 2.4 mg/dL (mild), 4 cats exhibiting serum creatinine of 2.4 mg/dL to 4.0 mg/dL (moderate), and 4 cats exhibiting serum creatinine of higher than 4.0 mg/dL (severe) when BPS administration was initiated. According to the report, improved kidney function was observed in all of the 4 subject cats exhibiting serum creatinine of 1.6 mg/dL to 2.4 mg/dL (mild) upon initiation of BPS administration. Among the 4 subject cats exhibiting serum creatinine of 2.4 mg/dL to 4.0 mg/dL (moderate), improved kidney function was observed in the 2 subject cats, and retained kidney function was observed in other 2 cats. Among the 4 subject cats exhibiting serum creatinine of higher than 4.0 mg/dL (severe), improved kidney function was observed in a cat, and temporary improvement, followed by impairment, was observed in other 3 cats. "Examination of therapeutic effects of beraprost sodium on feline chronic renal failure" indicates that feline CKD with lower severity can achieve higher effects of BPS to improve kidney function. From the viewpoint of clinical medicine, as described above, BPS was considered to exert higher effects on feline CKD at an earlier IRIS stage. In the human CKD, also, sufficient effects of BPS are observed only in minor conditions. When BPS immediate release tablets similar to RAPROS are administered to a patient with chronic renal failure, for example, effects of BPS are not observed at serum creatinine of 2.2 mg/dl or higher (Fujita et al., Vascular Biology & Medicine, 2006, Vol. 7, p. 281).

Based on the conventional findings, accordingly, it was impossible to predict that progression of CKD into IRIS stage 4 or kidney death of a cat would be inhibited or the overall survival rate or the observed survival rate would be improved by BPS administration.

It could therefore be helpful to provide a therapeutic method for a cat with CKD to inhibit progression of CKD into IRIS stage 4 or kidney death of a cat or to improve the overall survival rate or the observed survival rate by administering a therapeutic agent comprising, as an active ingredient, a compound represented by formula (I) to a specific cat with CKD.

SUMMARY

We thus provide:

(1) A therapeutic method for a cat with CKD to inhibit progression of CKD into IRIS stage 4 or kidney death of a cat with CKD by administering a therapeutic agent comprising, as an active ingredient, a compound represented by formula (I) to a cat with stage 3 or 4 CKD defined by the staging system established by the International Renal Interest Society (the IRIS staging) in an amount of 90 to 130 µg of the compound represented by formula (I) daily:

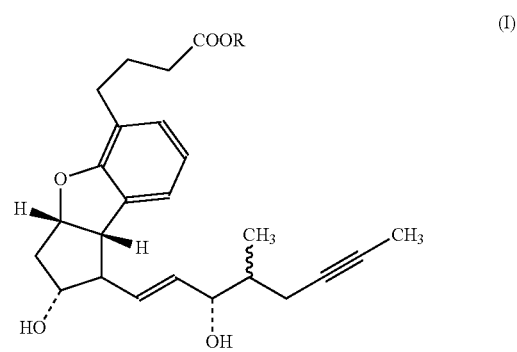

wherein R represents hydrogen or a pharmacologically acceptable cation.

(2) A therapeutic method for a cat with CKD to improve the overall survival rate or the observed survival rate of a cat with CKD by administering a therapeutic agent comprising, as an active ingredient, a compound represented by formula (I) to a cat with stage 3 or 4 CKD defined by the staging system established by the International Renal Interest Society (the IRIS staging) in an amount of 90 to 130 µg of the compound represented by formula (I) daily:

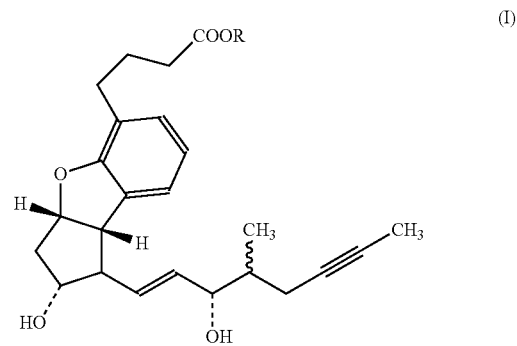

wherein R represents hydrogen or a pharmacologically acceptable cation.

(3) The therapeutic method according to (1) or (2), wherein the compound represented by formula (I) is beraprost sodium.

(4) The therapeutic method according to any of (1) to (3), wherein the cat having CKD with IRIS stage 3 or 4 exhibits body weight loss to less than 4.2 kg.

(5) The therapeutic method according to any of (1) to (4), wherein the cat having CKD with IRIS stage 3 exhibits serum creatinine of 2.9 mg/dL to 5.0 mg/dL and serum SDMA of 9.0 µg/dL or higher.

(6) The therapeutic method according to any of (1) to (4), wherein the cat having CKD with IRIS stage 4 exhibits serum creatinine of higher than 5.0 mg/dL and serum SDMA of 9.0 µg/dL or higher.

(7) The therapeutic method according to any of (1) to (5), wherein the therapeutic agent is administered to the cat having CKD with IRIS stage 3.

(8) The therapeutic method according to any of (1) to (7), wherein the cat having CKD with IRIS stage 3 or 4 satisfies the serum creatinine criterion of the IRIS staging criteria.

(9) The therapeutic method according to any of (1) to (8), wherein the compound represented by formula (I) is administered to the cat with CKD in an amount of 14.1 to 52.4 µg/kg body weight/day.

(10) The therapeutic method according to any of (1) to (9), wherein administration to the cat with CKD is performed twice daily.

(11) The therapeutic method according to any of (1) to (10), wherein administration to the cat with CKD is performed during or after feeding.

(12) The therapeutic method according to any of (1) to (11), wherein administration to the cat with CKD is performed in addition to a standard care for feline CKD.

(13) The therapeutic method according to (12), wherein the standard care is a therapeutic method defined by the guidelines from the International Society of Feline Medicine or the International Renal Interest Society.

(14) The therapeutic method according to any of (1) to (13), wherein the cat with CKD also has chronic heart failure, diabetes mellitus, pancreatitis, neoplasia, hyperthyroidism, hypertension, proteinuria, hypokalemia, hyperphosphatemia, or anemia.

(15) A therapeutic agent used for the therapeutic method according to any of (1) to (14).

(16) A compound represented by formula (I) used for the therapeutic method according to any of (1) to (14).

According to our therapeutic method, it is possible to inhibit progression into IRIS stage 4 or kidney death of a cat having CKD with IRIS stage 3 or 4 according to the staging system established by the International Renal Interest Society (the IRIS staging).

In addition, it is possible to improve the overall survival rate or the observed survival rate of a cat having CKD with IRIS stage 3 or 4.

When the cat having CKD with IRIS stage 3 or 4 exhibits body weight loss to less than 4.2 kg, stage progression can be inhibited or the overall survival rate or the observed survival rate can be improved more effectively.

When the cat having CKD with IRIS stage 3 or 4 exhibits serum creatinine of 2.9 mg/dL to 5.0 mg/dL and serum SDMA of 9.0 µg/dL or higher, stage progression can be inhibited or the overall survival rate or the observed survival rate can be improved more effectively.

Further, we provide a therapeutic agent used for the therapeutic method described above.

BRIEF DESCRIPTION OF THE DRAWINGS

FIG. 4 is a view showing changes in stage progression-free rates of cats having CKD with IRIS stage 2 in the BPS therapy group and in the No BPS therapy group.

FIG. 6 is a view showing changes in kidney survival rates of cats having CKD with IRIS stage 2 in the BPS therapy group and in the No BPS therapy group.

FIG. 9 is a view showing changes in overall survival rates of cats having CKD with IRIS stage 2 in the BPS therapy group and in the No BPS therapy group.

FIG. 10 is a view showing changes in overall survival rates of cats having CKD with IRIS stage 3 and having body weight of less than 4.2 kg in the BPS therapy group and in the No BPS therapy group.

DETAILED DESCRIPTION

Figure 1:
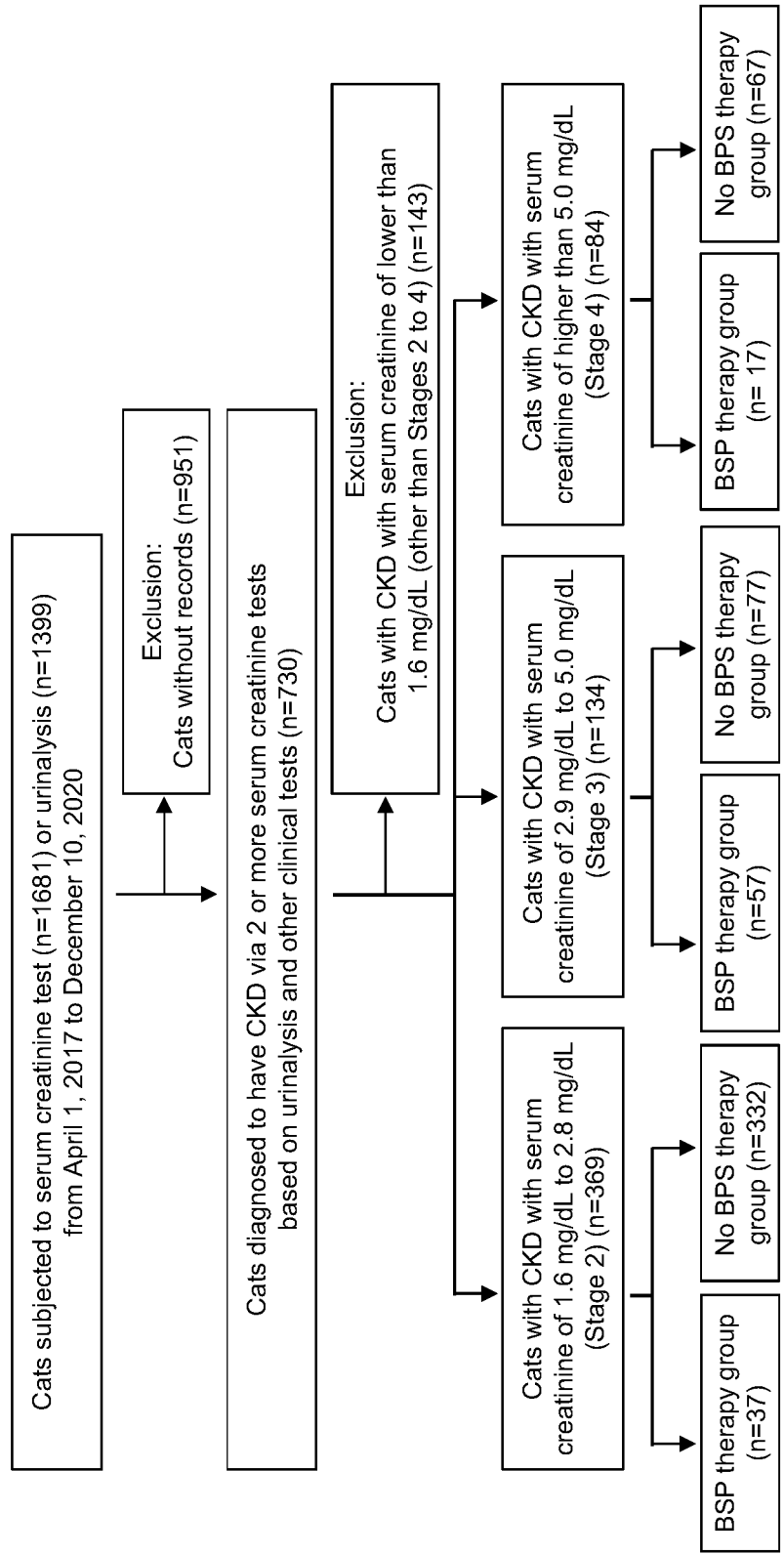
FIG. 1 is a test flow chart demonstrating a method of extracting data sets of subject cats.

Our therapeutic agent comprises a compound represented by general formula (I):

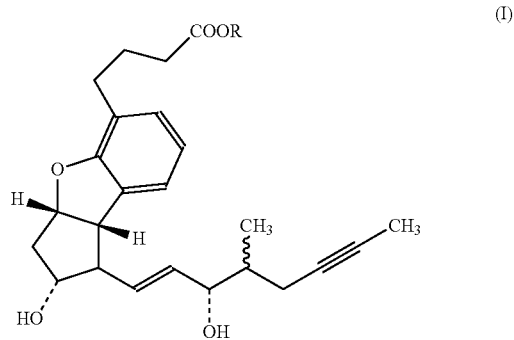

wherein R represents hydrogen or a pharmacologically acceptable cation.

Examples of pharmacologically acceptable cations include: alkali metals and alkaline earth metals such as sodium, potassium, and calcium; amines typified by mono-, di-, or trimethylamine, methylpiperidine, mono-, di-, or triethanolamine, and lysine; basic amino acids; and the like. Of these, sodium and potassium are particularly preferably used.

Further, among the compounds represented by formula (I), beraprost or pharmacologically acceptable salts thereof are preferably used. Of these, in addition to beraprost, BPS, which is a sodium salt of beraprost, or a potassium salt of beraprost is particularly preferably used. It should be noted that such substances are simply examples and are not exclusive examples.

Compounds represented by formula (I) are known and can be produced by known techniques described in, for example, JP H01-53672 B (1989), JP H07-5582 B (1985), JP H03-7275 A (1991), and JP H06-62599 B (1994).

Any of compounds represented by formula (I) can be used by itself or in combination of two or more.

Dose and Direction for Use

In our therapeutic method, a dose of the compound represented by formula (I) or beraprost sodium is 90 to 130 μg, and preferably 110 μg daily. When the compound represented by formula (I) is beraprost potassium, such compound can preferably also be used. A daily dose is 93 to 135 μg, and preferably 114 μg.

Body weights of cats with CKD vary among individuals. Thus, a dose is preferably determined per body weight. When the compound represented by formula (I) is beraprost sodium, for example, the compound can be administered while adjusting the dose to 12.6 to 57.7 μg/kg body weight/day, and preferably 14.1 to 52.4 μg/kg body weight/day. When the compound represented by formula (I) is beraprost potassium, the dose thereof is 13.1 to 59.9 μg/kg body weight/day, and preferably 14.6 to 54.5 μg/kg body weight/day.

While the frequency of administration to a cat per day is not particularly limited, in general, administration is performed 1 to 4 times daily, and preferably twice daily. If there are no particular problems in terms of side-effects, administration may be performed once daily. Alternatively, administration may be performed during feeding, and a larger number of administration frequency may be set.

The timing of administration during a day is not particularly limited, and administration is preferably performed after or during morning and evening feeding occasions. Further, a formula feed for cats with CKD can be supplemented with the therapeutic agent in advance and administered under a doctor's or veterinarian's guidance. The formula feed can be divided and administered at the same frequency as the frequency of daily feeding occasions.

BPS is composed of four stereoisomers, and its medicinal effect is mainly responsible for BPS-314d (sodium (+)-(1R,2R,3aS,8bS)-2,3,3a,8b-tetrahydro-2-hydroxy-1-[(E)-(3S,4S)-3-hydroxy-4-methyl-1-octen-6-ynyl]-1H-cyclopenta[b]benzofuran-5-butyrate) (H. Mizutani et al.). Therefore, therapeutic agents containing only BPS-314d, which is an active ingredient of BPS, are also preferably used. Regarding the plasma concentration of BPS-314d when BPS is administered, both AUC (area under the blood concentration time curve; the area of the part surrounded by the curve (blood drug concentration-time curve) showing the time course of blood concentration and the horizontal axis (time axis)) and Cmax (maximum drug concentration) are found to be almost ¼ in humans (Shimamura et al., J. Clin. Pharmacol., 2017, 57, 524-535) or rats (Matsumoto et al., Yakubutsu Dotai (Pharmacokinetics), 1989, 4(6), 713-725), and such tendency is considered to be similar in cats. Therefore, when a preparation containing an active body of BPS (e.g., BPS-314d) alone is administered, the effective dose per day of BPS-314d is 22.5 to 32.5 g, and preferably 27.5 μg, which is ¼ the dose of BPS. Further, an active body of beraprost potassium (potassium (+)-(1R,2R,3aS,8bS)-2,3,3a,8b-tetrahydro-2-hydroxy-1-[(E)-(3S,4S)-3-hydroxy-4-methyl-1-octen-6-ynyl]-1H-cyclopenta[b]benzofuran-5-butyrate) is also particularly preferably used by itself. The daily dose in this case is 23 to 34 μg, and preferably 28 to 29 μg.

Various dosage forms can be adopted for drugs used in our therapeutic method. In oral administration, specific examples of dosage forms include tablets, chewable tablets, powders, fine granules, granules, liquids, syrups, capsules, pills, and sprays. Alternatively, molded products can be film-coated, sugar-coated, or encapsulated. Preferable examples include liquids, tablets, powders, fine granules, granules, liquids, syrups, and capsules. Alternatively, a drug may be administered parenterally in the form of a disinfection solution or the like, or another solute such as a sufficient amount of sodium chloride or glucose to make an isotonic solution, may be used.

The therapeutic agent can be used in various forms such as injection preparations, nasal drops, ear drops, eye drops, transdermal agents, ointments, or suppositories, in addition to the therapeutic agents described above. In accordance with properties of each agent, release of each agent can be controlled to prepare a sustained-release or delayed-release agent. For example, our agent can be provided with a controlled-release function in accordance with an conventional technique and administered via extensive parenteral routes in the form of an implanted controlled-release pump (e.g., Alzet mini pump) or the like.

Oral Immediate Release Tablet

In addition to the therapeutic agent that has been approved to be manufactured and commercialized as RAPROS (trademark) in Japan, therapeutic agents for cats that can be preferably used are therapeutic agents demonstrated to have bioequivalence to RAPROS (trademark) based on, for example, pharmacokinetic studies on elution behavior or in a clinical setting performed in accordance with the methods described in, for example, the "Guideline for Bioequivalence Studies of Generic Veterinary Products," the "Guideline on the conduct of bioequivalence studies for veterinary medicinal products (EMA/CVMP/016/2000)," and the "Guideline for Bioequivalence Studies of Generic Products." For example, such therapeutic agents can be prepared in the manner described below.

As excipients, lactose and starch are introduced into an agitation granulator, and granules are produced with agitation with the addition of a solution of BPS and a binder (hypromellose) prepared in advance. The granules are fractured, dried, and size-regulated to prepare dry granules, a lubricant (magnesium stearate) is added to the dry granules, the resultant is mixed in a mixer, and uncoated tablets are then obtained using a rotary tablet press machine. The uncoated tablets are introduced into a coater and sprayed with a coating solution prepared in advance (polyethylene glycol, hypromellose) to coat the uncoated tablets, and carnauba wax is then added to prepare film-coated tablets.

The therapeutic agent may contain additives such as excipients, lubricants, binders, stabilizers, and solubilizing agents. The additives are not particularly limited as long as they are pharmacologically acceptable. Examples of excipients include lactose, saccharose (sucrose), D-mannitol, sorbitol, xylitol, crystalline cellulose, corn starch, gelatin, polyvinyl pyrrolidone, dextran, polyethylene glycol (hereinafter, abbreviated as PEG; another name: Macrogol) 1500, PEG 4000, PEG 6000, PEG 20000, polyoxyethylene polyoxypropylene glycol (PEP 101 (trademark) and Pluronic (trademark)) and the like. Further, examples of lubricants include magnesium stearate, calcium stearate, talc and the like; examples of binders include hydroxypropylcellulose, hydroxypropylmethylcellulose, methylcellulose, stearic acid, propylene glycol and the like; examples of stabilizers include butylhydroxytoluene, butylhydroxyanisole, ascorbic acid, propyl gallate, dibutylmethylphenol, sodium thiosulfate and the like; and examples of solubilizing agents include polyethylene hydrogenated castor oil, polyethyleneglycol monostearate and the like. The amounts of these additives mixed are selected as appropriate depending on the type and purpose thereof.

Further, acrylic acid polymer, polyvinyl alcohol, hydroxypropyl cellulose, various commercially available premix coating agents and the like can be used as tablet-coating agents.

In addition to the process described above, a continuous production process can be employed as a method of preparing an oral therapeutic agent, and a production process is not particularly limited.

Tablet Diameter

A form of a therapeutic agent comprising compound (I) that can be used and is not particularly limited, and a preferable example is a tablet. A tablet diameter is important because it significantly affects drug intake for cats. Such diameter is 4.5 to 10.5 mm, preferably 4.5 to 7.5 mm, and more preferably 5.5 to 6.5 mm. When grains or fine grains with diameters of 10 to 1,000 μm are to be filled in a capsule to easily mix the therapeutic agent with a feed, a size of a capsule is preferably 4.5 to 6.0×11.0 to 17.5 mm (inner diameter×full-length after filling) so that the capsule can be administered by itself.

Oral Sustained-Release Therapeutic Agent

Sustained-release therapeutic agents are those that delay the release of active ingredients from therapeutic agents to reduce the number of doses, and keep the active ingredient concentration in the blood constant for a long period of time to avoid side effects, as described in the Pharmaceutical Glossary of the Pharmaceutical Society of Japan.

Sustained-Release Therapeutic Agent

As BPS therapeutic agents used for treatment of cats, it is possible to use sustained-release therapeutic agents, and, in particular, oral sustained-release therapeutic agents.

Examples of sustained-release therapeutic agents for oral administration include single-unit and multiple-unit sustained-release therapeutic agents. Many of single-unit agents gradually release drugs while the dosage form is maintained in the gastrointestinal tract. Examples of single-unit agents include wax matrix, gradumet, repetab, lontab, spantab and the like. As for multiple-unit agents, administered tablets or capsules are rapidly disintegrated to release granules, and the released granules show sustained-release properties. Examples of multiple-unit agents include spacetab, spansule, granule and the like. Further, in terms of release control mechanism, they are divided into reservoir agents and matrix agents. Reservoir agents are obtained by coating drug-containing tablets or granules with polymer coatings, and the drug release rate is determined by the properties and thickness of the coating. Repetab, spacetab, spansule, and granule belong to reservoir agents. Matrix agents are obtained by dispersing drugs in bases such as polymers or waxes, and the release rate is determined by the diffusion rate of drug molecules in the matrix. Wax matrix, gradumet, lontab, spantab and the like belong to matrix agents. Various sustained-release therapeutic agents can be used, regardless of the method of sustained-release, as long as they have the release characteristics described above.

Among the above, the sustained-release therapeutic agents that can be used are not particularly limited. For example, WO98/41210 and WO2004/103350 disclose BPS sustained-release therapeutic agents comprising a hydrogel base as a release control component of BPS. The BPS sustained-release therapeutic agents produced by these methods can also be used.

As another form of a sustained-release therapeutic agent comprising BPS, WO 2004/103350 discloses an oral sustained-release pharmaceutical composition comprising a plurality of granules with particle sizes of 1000 μm or less. Such therapeutic agent can also be used.

Flavored Tablet

Cats with CKD are known to lose their appetites. Accordingly, it is possible to increase their appetites by supplementing the therapeutic agent with a flavor or taste preferred by cats.

As described above, various dosage forms and administration methods can be adopted. When a dosage form or administration method different from that of an oral therapeutic agent, RAPROS (trademark) (Toray Industries, Inc.), is to be adopted, it is preferable to adjust the amount of drug exposure to cats at the equivalent level. Such equivalence may be determined primarily based on AUC. When blood kinetics varies depending on a type of CKD, such variation is preferably taken into consideration to evaluate equivalence.

When the therapeutic agent comprising, as an active ingredient, the compound represented by formula (I), for example, a therapeutic agent comprising BPS is to be administered, a tablet of RAPROS (trademark) (Toray Industries, Inc.) (BPS content: 55 μg/tablet) may be administered twice daily (2 tablets in total) so that 110 μg of BPS would be administered daily.

Target Feline CKD

The methods of IRIS diagnosis and staging described in the Background Art section can be employed as the methods of diagnosis and staging of the target feline CKD.

Specifically, patient animals are diagnosed to have feline CKD when at least one of the following indicators is persistently observed on the basis of the medical history and the results of physical examination, clinical examination, diagnostic imaging, and histopathological examination of patient animals in stable conditions. The indicators are elevated serum creatinine or serum SDMA, persistent elevation in serum SDMA to >14 μg/dL, renal proteinuria accompanied by the persistent UPC ratio of >0.4, the urine specific gravity of <1.035, inappropriate tubular loss of potassium, bicarbonate, glucose or amino acid, renal cyst, urolith, and renal tumor. Subsequently, the IRIS staging can be performed as described below on the basis of assessment of serum creatinine or serum SDMA or preferably serum creatinine and serum SDMA via two or more hospital visits: stage 1: serum creatinine of lower than 1.6 mg/dL or serum SDMA of lower than 18 μg/dL or preferably serum creatinine of lower than 1.6 mg/dL and serum SDMA of lower than 18 μg/dL; stage 2: serum creatinine of 1.6 to 2.8 mg/dL or serum SDMA of 18 to 25 μg/dL or preferably serum creatinine of 1.6 to 2.8 mg/dL and serum SDMA of 18 to 25 μg/dL; stage 3: serum creatinine of 2.9 to 5.0 mg/dL or serum SDMA of 26 to 38 μg/dL or preferably serum creatinine of 2.9 to 5.0 mg/dL and serum SDMA of 26 to 38 g/dL; and stage 4: serum creatinine of higher than 5.0 mg/dL or serum SDMA of higher than 38 μg/dL or preferably serum creatinine of higher than 5.0 mg/dL and serum SDMA of higher than 38 μg/dL.

In this description, serum creatinine, serum SDMA, and body weight values are rounded to 2 significant figures.

In the IRIS diagnostic method, it is necessary that the diagnostic criteria be persistently satisfied. In clinical practice, however, a decision is often expected to be made through one hospital visit. Accordingly, a patient animal can be diagnosed to have CKD if the patient animal satisfies the diagnostic criteria for the first time. In the IRIS staging, either serum creatinine or serum SDMA, and preferably both serum creatinine and serum SDMA, should be examined through at least 2 hospital visits. However, it is possible to treat a subject that satisfies the criteria through a single hospital visit in the same manner as in a subject that is diagnosed to have CKD through 2 hospital visits in consideration of operation in clinical practice.

It is possible to determine the stage of the target feline CKD based on serum creatinine by itself, and the determined stage is not necessarily consistent with the IRIS stage. The range of serum creatinine adopted in such an instance is the same as that adopted in the IRIS staging. CKD is diagnosed as stage 2 at serum creatinine of 1.6 to 2.8 mg/dL, stage 3 at serum creatinine of 2.9 to 5.0 mg/dL, and stage 4 at serum creatinine of higher than 5.0 mg/dL.

Concerning the cats with CKD in accordance with the staging based only on serum creatinine, progression from stage 3 into stage 4 or progression from stage 3 or stage 4 into kidney death can be inhibited by the method. Further, the overall survival rate or the observed survival rate of cats having CKD with stage 3 or 4 can be improved.

Further, the method is more preferably employed to inhibit progression of IRIS stage 3 CKD into stage 4 or improve the overall survival rate or the observed survival rate when cats having CKD with IRIS stage 3 have serum creatinine of 2.9 mg/dL to 5.0 mg/dL and serum SDMA of 9.0 μg/dL or higher.

When cats having CKD with IRIS stage 4 have serum creatinine of higher than 5.0 mg/dL and serum SDMA of 9.0 μg/dL or higher, in addition, the method is more preferably used to inhibit kidney death or improve the overall survival rate or the observed survival rate.

The therapeutic method is effective on stage 3 and stage 4 CKD. Concerning cats having CKD with stage 2, however, inhibition of progression into stage 4 or improvement in the overall survival rate or the observed survival rate is not observed.

As described in the Background, it is impossible to predict that higher effects would be achieved in severe cases of chronic nephropathy than in mild cases based on the conventional finding on BPS administration in treatment of feline CKD. That is, a feature such that higher effects would be achieved in severe cases is considered to be an important feature.

While a BPS sustained-release therapeutic agent delays transition of treatment of patients with primary glomerular disease or nephrosclerosis into dialysis and kidney death caused by transition into dialysis or transplantation in human patients with CKD, such effects are limited to the mildest case exhibiting serum creatinine of 2.0 mg to lower than 3.0 mg/dL when administration was initiated, and no effects were observed in cases exhibiting serum creatinine of 3.0 mg/dl or higher.

As described above, it was impossible to predict that particularly significant effects would be observed in terms of inhibition of IRIS stage progression, inhibition of kidney death, and improvement in the survival rate in more severe cases of cats.

Malnutrition

The therapeutic method is particularly effective for cats with CKD suffering from malnutrition. Examples of malnutrition in cats with CKD include body weight loss and decrease in body build, muscle weight, nutritional intake, and serum protein levels.

In particular, body weight loss is an effective indicator of cats with CKD suffering from malnutrition. Specifically, life prognosis in cats with CKD having body weight of less than 4.2 kg is poorer than that in cats having body weight of 4.2 kg or more (L. M. Freeman et al.). Accordingly, body weight of less than 4.2 kg is an important criterion to diagnose malnutrition. Effects of inhibition of stage progression, inhibition of kidney death, and improvement in the survival rate are more remarkable in the cases of IRIS stage 3 or 4 having body weight of less than 4.2 kg. The effects are more remarkable in the cases of advanced malnutrition having body weight of less than 3.5 kg.

Decrease in body weight by 5% or more in 6 months is a useful criterion to determine that a subject has body weight loss or malnutrition. Such decrease is particularly useful when the body weight is naturally less than 4.2 kg or less than 3.5 kg and it is difficult to determine that body weight loss is caused by the CKD.

As another indicator of malnutrition, it is possible to use lowering of the 9-point-scale body conditioning score (BCS) serving as an indicator of decrease in body build or muscle weight to score 3 or lower or lowering of the 4-point-scale muscle conditioning score (MCS) to mild muscle wasting or lower. In addition, it is possible to use lowering of the serum protein level or the serum albumin level to a level lower than the standard level or lowering of the lymphocyte count to a level lower than the standard level as an indicator of malnutrition. It is also possible to diagnose malnutrition with the use of such indicators in combination.

Primary Disease

The cause of feline CKD has not yet been fully elucidated at present, and aging is known to be a cause of feline CKD. Other diseases as exemplified below are known to cause feline CKD, although it is often impossible to identify the cause.

Specifically, examples of causes or causative diseases of the CKD include chronic tubulointerstitial nephritis, chronic glomerulonephritis, juvenile kidney dysplasia, polycystic kidney disease, nephrolithiasis, urolithiasis, obstructive uropathy, acute kidney insufficiency, diabetic nephropathy, hypercalcemic nephropathy, kidney lymphoma, amyloid nephropathy, chronic pyelonephritis, chronic viral infection, systemic inflammatory syndrome, toxic disorders, and chronic malnutrition. Examples of chronic glomerulonephritis types include membranous nephropathy, mesangial proliferative glomerulonephritis, and membranoproliferative glomerulonephritis.

It is apparent that IRIS diagnosis of feline CKD is performed based on, for example, serum creatinine, serum SDMA, and urine specific gravity. Accordingly, the CKD is defined as a common pathological condition regardless of the primary disease. The method is effective regardless of the causative disease.

Determination of Kidney Death

The IRIS staging for feline CKD does not define the pathological stage at which a patient cat has lost almost all kidney functions and would die in a few days without kidney replacement therapy such as dialysis or kidney transplantation. The IRIS guidelines on acute kidney insufficiency, however, indicate that "a patient may die within 5 to 10 days despite appropriate conservative therapy without kidney replacement therapy if serum creatinine is higher than 10.0 mg/dL." In accordance therewith, it is possible to define kidney death when serum creatinine is increased to higher than 10.0 mg/dL. It is possible to inhibit kidney death of cats having CKD with stage 3 or 4.

Overall Survival Rate or Observed Survival Rate

The term "overall survival rate" is synonymous with the term "observed survival rate," and such term indicates a survival rate regardless of the cause of death including death resulting from complications and comorbidities that arise as the kidney function is impaired. It is possible to improve the overall survival rate or the observed survival rate.

In feline CKD and, in particular, stage 2 or advanced CKD, kidney function to filter low-molecular-weight substances is irreversibly impaired. Serum creatinine and serum SDMA accumulate in the blood as the kidney function to filter low-molecular-weight substances is impaired and levels thereof are gradually elevated. Thus, such levels can be used as indicators which indicate that the kidney function to filter low-molecular-weight substances is impaired.

On the other hand, as various functions including the kidney function to filter low-molecular-weight substances are impaired, the cardiovascular functions are damaged (J. L. Pouchelon et al.). Accordingly, many cats with CKD die of heart failure instead of progression of the CKD. In addition, the International Society of Feline Medicine provides, in the guidelines on treatment and management of feline CKD, examples of complications/comorbidities associated with worsening of feline CKD such as hypertension, proteinuria, hypokalemia, hyperphosphatemia, urinary tract infection, anemia, and CKD-mineral bone disorder (A. H. Sparkes et al.), and such complications/comorbidities are known to cause death because of feline CKD.

In clinical practice, impaired kidney function caused by progression of the chronic kidney disease is often associated with the complications/comorbidities, and it is often impossible to identify the cause of death in fatal cases. In evaluation of therapeutic methods for feline CKD, accordingly, the overall survival rate or the observed survival rate including all the deaths caused by other factors such as the complications/comorbidities in addition to the deaths caused by progression of the CKD can be the most important indicator. According to the therapeutic method, it is possible to improve the overall survival rate or the observed survival rate of cats with IRIS stages 3 and 4 CKD.

Complications and Comorbidities in Target Cats with CKD

As described above, feline CKD is often associated with complications/comorbidities such as hypertension, proteinuria, hypokalemia, hyperphosphatemia, urinary tract infection, anemia, and CKD-mineral bone disorder. Cats with such complications/comorbidities associated with the CKD can be the targets. Complications/comorbidities are diagnosed as follows: hypertension when the systolic blood pressure is measured to be 160 mmHg or higher by the blood pressure test; proteinuria when urine protein is measured to be 100 mg/dL or higher by the urine dipstic test; hypokalemia when potassium is measured to be lower than 3.5 mEq/L by the blood chemistry test; hyperphosphatemia when phosphorus is measured to be 6.0 mg/dL or higher by the blood chemistry test; and anemia when hematocrit is measured to be lower than 30% by the blood count test.

Further, it is possible to treat kidney diseases associated with diseases often observed in cats such as hyperthyroidism, pancreatitis, neoplasia, and chronic heart failure. The method can be effectively used for cats with diabetic nephropathy that have developed diabetes mellitus associated with the CKD.

Existing Therapy that can be Employed in Combination

The therapeutic method can be employed in combination with an existing therapeutic method or a standard care for feline CKD. The therapeutic method performed in combination with a common standard care for the CKD, which is the therapeutic method defined by the guidelines from the International Society of Feline Medicine and the International Renal Interest Society, is particularly effective.

The guidelines from the International Society of Feline Medicine exemplify, as therapeutic agents for feline CKD, phosphate binders, active vitamin D3 analogs, calcium channel blockers, βblockers, erythrocyte-stimulating agents, angiotensin-converting enzyme inhibitors, angiotensin receptor blockers, nurokinin-1 receptor antagonists, nonadrenergic and specific serotonergic antidepressants, 5-hydroxytryptamine receptor 4 agonists, 5-hydroxytryptamine receptor 3 antagonists, histamine-2 receptor blockers, and proton pump inhibitors, and such therapeutic agents can be used.

Among them, an angiotensin-converting enzyme inhibitor, benazepril hydrochloride, and an angiotensin receptor blocker, telmisartan, are extensively used as therapeutic agents for proteinuria in feline CKD. Also, enalapril, lisinopril, losartan, spironolactone, omega-3 fatty acids, and amlodipine are reported as therapeutic agents for feline proteinuria (Harley L, Langston C, Proteinuria in dogs and cats, Can. Vet. J., 2012; 53(6): 631-638).

However, such therapeutic agents are not intended to normalize the pathological conditions of cats with CKD or improve the survival rate, and such therapeutic agents are used to improve symptoms characteristic of cats with CKD or abnormal laboratory values. For example, erythrocyte-stimulating agents may be used for treatment of anemia that is often observed in cats with CKD, and angiotensin-converting enzyme inhibitors, angiotensin receptor blockers, calcium channel blockers, or βblockers may be used for treatment of hypertension associated with kidney disease. In the aforementioned guidelines, adequate therapeutic methods and medicines to be used in accordance with the pathological conditions of the cats with CKD are defined. The guidelines point out that use of drugs for cases without symptoms may worsen the kidney disease.

Examples of angiotensin-converting enzyme inhibitors that can be used include, in addition to the benazepril hydrochloride described above, captopril, enalapril, imidapril, lisinopril, perindopril, ramipril, alacepril, moexipril, fosinopril, quinapril, and a pharmacologically acceptable salt of any thereof.

Examples of angiotensin receptor blockers include, in addition to the telmisartan described above, losartan, eprosartan, candesartan cilexetil, valsartan, irbesartan, tasosartan, olmesartan, zolasartan, mifasartan, folasartan, and, according to need, a metabolically active substance (e.g., candesartan) and a pharmacologically acceptable salt of any thereof.

Alternatively, angiotensin-converting enzyme inhibitors and angiotensin receptor blockers may be used in combination, or angiotensin-converting enzyme inhibitors or angiotensin receptor blockers may be used in combination with aldosterone antagonists, calcium channel blockers, βblockers, or various diuretic agents.

In addition to the therapeutic methods defined in the guidelines from the International Society of Feline Medicine and the International Renal Interest Society, drugs that are commonly used for treatment of feline kidney disease described below can be used in combination.

In Japan, for example, carbon based sorbents that remove causative substances of uremia from the gastrointestinal tract have been approved as drugs for veterinary use and extensively used in a clinical setting for the purpose of treatment of feline uremia. The therapeutic method is also effective for cases that have received treatment with carbon based sorbents. Specific examples include spherical adsorptive carbon granules such as Covalzin (trademark) for cats and Kremezin (trademark) for humans, and active carbons commercialized as veterinary nutraceuticals/supplements and veterinary/prescription diets.

Also, body weight loss in feline CKD is associated with the lowered survival rate. Accordingly, a ghrelin receptor agonist, capromorelin, has been extensively used as a therapeutic agent for body weight loss. Other examples of therapeutic agents include anamorelin, ipamorelin, tavimorelin, and a pharmacologically acceptable salt of any thereof.

Veterinary/prescription diets and subcutaneous fluid therapy for CKD can also be employed in combination.

Measurement Method of Various Parameters

Measurement Method of Serum Creatinine

A measurement method of serum creatinine is not particularly limited, and, in general, it is performed by an enzymatic method or the Jaffe method. Specifically, measurement is performed with the use of commercially available hematology analyzers for veterinary use such as Fuji Dry Chem N X700V (FUJIFILM VET Systems Co., Ltd.), Catalyst One (IDEXX Laboratories, Inc.), Spotchem D-concept (Arkley), Vetscan VS2 (Abaxis, Inc.), and Element DC5X (Heska Corp.), or measurement is performed at clinical research centers such as IDEXX Laboratories, Inc., FUJIFILM VET Systems Co., Ltd., Unitech Diagnostics, Inc., Abaxis, Inc., Heska Corp., and Abot Laboratories, Inc.

Alternatively, a human measurement method of serum creatinine can also be employed. Measurement is preferably performed by an enzymatic method. Specifically, in addition to Cygnus Auto CRE (Shino-Test Corp.) commercialized as a clinical test drug, L-type Wako CRE-M (FUJIFILM Wako Pure Chemical Corp.), Pure Auto S CRE-N(Sekisui Medical Co., Ltd.), Serotec CRE-N(Serotec Co., Ltd.), Aqua-auto Kainos CRE-III plus (Kainos Laboratories, Inc.), Cica Liquid-N CRE (Kanto Chemical Co., Inc.) and the like are used. Any clinical test drugs that use the enzymatic method can be used without any particular limitation.

Measurement Method of Serum SDMA

A measurement method of serum SDMA is not particularly limited, and, in general, it is performed by an enzymatic method, liquid chromatography-mass spectrometry (LC-MS), or high performance liquid chromatography (HPLC). Specifically, measurement is performed with the use of a commercially available hematology analyzer for veterinary use such as Catalyst One (IDEXX Laboratories, Inc.), or measurement is performed at clinical research centers such as IDEXX Laboratories, Inc., FUJIFILM VET Systems Co., Ltd., Unitech Diagnostics, Inc., Abaxis, Inc., Heska Corp., and Abot Laboratories, Inc.

Measurement Method of Urine Specific Gravity

A measurement method of urine specific gravity is not particularly limited, and, in general, it is performed by refractometry. Specifically, measurement is performed with the use of a commercially available urine specific gravity refractometer for veterinary use such as Pocket Urine Specific Gravity Refractometer PAL-CAT (ATAGO Co., Ltd.), Pocket Urine Specific Gravity Refractometer PAL-DOG & CAT (ATAGO Co., Ltd.), MASTER-Urine Specific Gravity Refractometer for dogs and cats (ATAGO Co., Ltd.), and VetScan UA (Abaxis, Inc.), or measurement is performed at clinical research centers such as IDEXX Laboratories, Inc., FUJIFILM VET Systems Co., Ltd., Unitech Diagnostics, Inc., Abaxis, Inc., Heska Corp., and Abot Laboratories, Inc.

Also, a urine specific gravity refractometer for human use can be used. Use of a correction formula: feline urine specific gravity level=(0.846×measured value)+0.154, is preferable. Specifically, Pocket Urine Specific Gravity Refractometer PAL-09S (ATAGO Co., Ltd.), MASTER-SUR/Ja (ATAGO Co., Ltd.) and the like may be used, and any refractometer may be used as long as measurement is performed by refractometry.

EXAMPLES

Next, our methods will be described in more detail while showing Examples and Comparative Examples. However, this disclosure is not limited by these examples.

Example 1: Preparation of Beraprost Sodium Tablets

Drugs to be administered to the cats in the examples and the comparative examples of the present application were prepared in the form of film-coated tablets each containing 55 μg of beraprost sodium (BPS) as the compound represented by formula (I) in the manner described below.

As excipients, lactose and starch were introduced into an agitation granulator, and granules were produced with agitation with the addition of a solution of BPS and a binder (hypromellose) prepared in advance. The granules were fractured, dried, and size-regulated to prepare dry granules, a lubricant (magnesium stearate) was added to the dry granules, the resultant was mixed in a mixer, and uncoated tablets were then obtained using a punch and a die (6 mm, 8 R) in a rotary tablet press machine. The uncoated tablets were introduced into a coater and sprayed with a coating solution prepared in advance (polyethylene glycol, hypromellose) to coat the uncoated tablets, and carnauba wax was then added to prepare film-coated tablets.

Example 2

Figure 2:
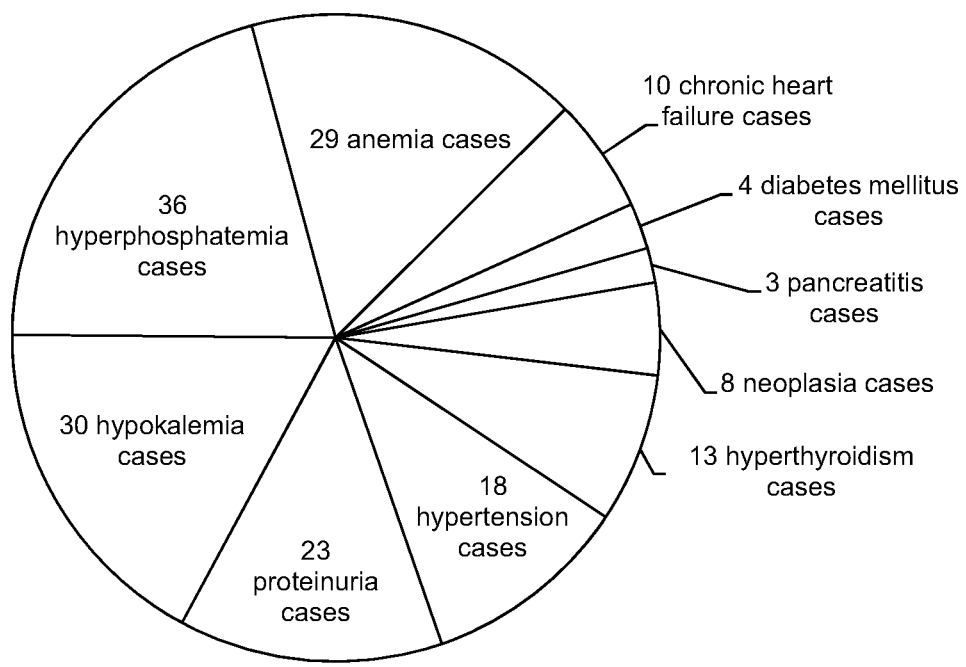
FIG. 2 is a view showing classification of complications and comorbidities of subject cats.

To compare the periods before progression of feline CKD into stage 4 with BPS therapy and without BPS therapy, the following retrospective observation studies were performed. The studies were performed at Ichikawa General Hospital, Kariya Animal Hospital, Inc., that had adopted the electronic chart system for veterinary hospitals, Ahmics (trademark) (PetCommunications Co., Ltd.), and completely eliminated the use of paper charts before 2017. In this hospital, all-encompassing information concerning medical treatment such as test data, death records, and drug prescription records of all patient animals have been managed by the electronic chart system. The data sets of the subject cats were extracted in the manner as shown in FIG. 1. Specifically, the data sets of 1,681 cats subjected to the serum creatinine test and the data sets of 1,399 cats subjected to the urinalysis from Apr. 1, 2017 to Dec. 10, 2020 were extracted. Among them, by excluding 951 cats without records, the data sets of 730 cats that were diagnosed to have CKD as a result of serum creatinine tests at least two times, urinalysis, and other clinical tests were extracted. Among them, the data sets of 134 cats diagnosed to have CKD exhibiting serum creatinine of 2.9 mg/dL to 5.0 mg/dL (stage 3) in accordance with the method defined by the IRIS staging were extracted and subjected to the analysis. All the cats subjected to serum SDMA measurement exhibited serum SDMA of 9 μg/dL or higher, and some of them were found to have developed chronic heart failure, diabetes mellitus, hyperthyroidism, pancreatitis, neoplasia, hypertension, proteinuria, hypokalemia, hyperphosphatemia, or anemia (FIG. 2).

Based on the drug prescription records, cats were divided into two groups: a BPS therapy group consisting of 57 cats; and a BPS therapy-free group consisting of 77 cats, and the baseline characteristics and the periods before progression into stage 4 were compared and analyzed retrospectively. To the cats in the BPS therapy group, BPS drugs for veterinary use, RAPROS (trademark) (Toray Industries, Inc.), were administered while adjusting the amount of BPS to 14.1 to 52.4 μg/kg body weight/day and the median to 29.1 μg/kg body weight/day twice daily during or after morning and evening feeding occasions. Other than BPS administration, common therapy for feline chronic kidney insufficiency was performed and no significant differences were observed in such common therapy between groups. Progression into stage 4 was examined by the method defined by the IRIS staging. Specifically, progression into stage 4 was determined based on serum creatinine or serum SDMA measured to be higher than 5.0 mg/dL or higher than 38 μg/dL, respectively, via two or more hospital visits. By designating progression into stage 4 as the outcome, the start date of treatment as the point of origin for the cats in the BPS therapy group, and the start date of observation as the point of origin for the cats in the No BPS therapy group, the periods (months) before the outcome was observed were recorded. In analysis, the 3-year stage progression-free rates (%) of the BPS therapy group and of the No BPS therapy group, the standard errors thereof, the 95% confidence intervals, and the comparison of the 3-year stage progression-free rates (%) between the groups were calculated. The periods (months) before progression into stage 4 of the BPS therapy group and of the No BPS therapy group and the outcomes thereof were analyzed by Kaplan-Meier analysis to show curves demonstrating changes in the stage progression-free rate relative to the observational period (months). As a case summary, progression into stage 4, discontinuation, and the overall number were demonstrated. The average period (months) before progression into stage 4, the standard error thereof, the 95% confidence intervals, the medians and the standard errors thereof, the 95% confidence intervals, and the comparison of the average stage progression-free periods were calculated. Differences in the stage progression-free rates were assessed by the log rank test, the Cochran-Mantel-Haenszel test, by setting significant level at a two-tailed P-value of <0.05.

Figure 3:
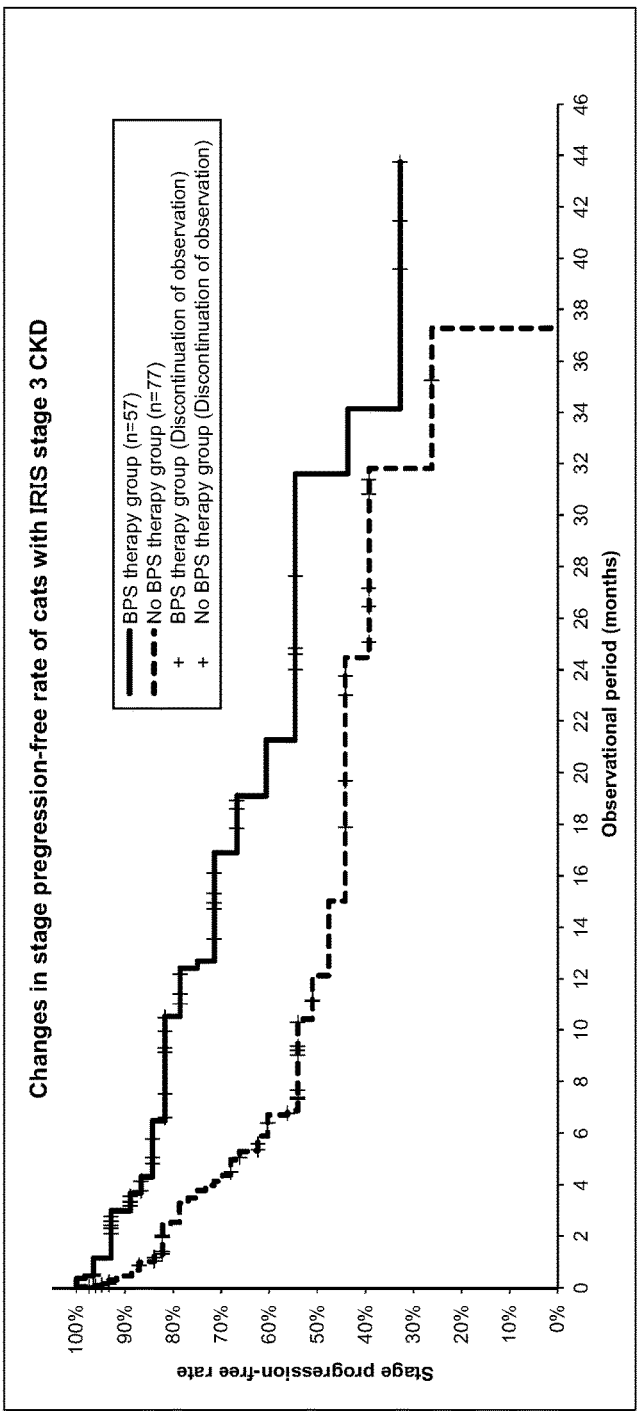
FIG. 3 is a view showing changes in stage progression-free rates of cats having CKD with IRIS stage 3 in the BPS therapy group and in the No BPS therapy group.

No difference that would affect the results of analysis was observed in baseline characteristics between the BPS therapy group and the No BPS therapy group. Concerning the BPS therapy group, the 3-year stage progression-free rate (%) was 32.7, the standard error thereof was 13.5, and the 95% confidence interval was 6.3 to 59.1. Concerning the No BPS therapy group, in contrast, the 3-year stage progression-free rate (%) was 26.2, the standard error thereof was 12.0, and the 95% confidence interval was 2.7 to 49.7. The 3-year stage progression-free rate (%) of the BPS therapy group was 1.25 times that of the No BPS therapy group. The results of Kaplan-Meier analysis demonstrated that the average period (months) before progression into stage 4 of the BPS therapy group was 26.5, the standard error thereof was 3.0, the 95% confidence interval was 20.6 to 32.3, the median thereof was 31.6, the standard error thereof was 9.4, and the 95% confidence interval was 13.1 to 50.1. In contrast, the results demonstrated that the average period (months) before progression into stage 4 of the No BPS therapy group was 17.8, the standard error thereof was 2.3, the 95% confidence interval was 13.3 to 22.3, the median thereof was 12.1, the standard error thereof was 5.2, and the 95% confidence interval was 1.9 to 22.4. The average stage progression-free period of the BPS therapy group was 1.49 times that of the No BPS therapy group. A P value indicating a difference in the stage progression-free rate between the groups was 0.0119. That is, effects of BPS administration to inhibit progression into stage 4 were observed in cats with CKD that had exhibited serum creatinine of 2.9 mg/dL to 5.0 mg/dL (stage 3) before initiation of administration (FIG. 3).

Comparative Example 1

In the studies described in Example 2, as shown in FIG. 1, the data sets of 369 cats diagnosed to have CKD exhibiting serum creatinine of 1.6 mg/dL to 2.8 mg/dL (stage 2) in accordance with the method defined by the IRIS staging were extracted and analyzed.

Based on the drug prescription records, cats were divided into two groups: a BPS therapy group consisting of 37 cats; and a BPS therapy-free group consisting of 332 cats, and the baseline characteristics and the periods before progression into stage 4 were compared and analyzed retrospectively. To the cats in the BPS therapy group, BPS drugs for veterinary use, RAPROS (trademark) (Toray Industries, Inc.), were administered while adjusting the amount of BPS to 18.5 to 42.3 μg/kg body weight/day and the median to 26.5 μg/kg body weight/day twice daily during or after morning and evening feeding occasions. Progression into stage 4 was examined by the method defined by the IRIS staging. Specifically, progression into stage 4 was determined based on serum creatinine or serum SDMA measured to be higher than 5.0 mg/dL or higher than 38 μg/dL, respectively, via two or more hospital visits. By designating progression into stage 4 as the outcome, the start date of treatment as the point of origin for the cats in the BPS therapy group, and the start date of observation as the point of origin for the cats in the No BPS therapy group, the periods (months) before the outcome was observed were recorded. In analysis, the 3-year stage progression-free rates (%) of the BPS therapy group and of the No BPS therapy group, the standard errors thereof, the 95% confidence intervals, and the comparison of the 3-year stage progression-free rates (%) between the groups were calculated. The periods (months) before progression into stage 4 of the BPS therapy group and of the No BPS therapy group and the outcomes thereof were analyzed by Kaplan-Meier analysis. On the basis thereof, progression into stage 4, discontinuation, and the overall number were demonstrated as a summary of cases. The average period (months) before progression into stage 4, the standard error thereof, the 95% confidence interval, the median and the standard error thereof, the 95% confidence interval, and the comparison of the average stage progression-free rates were demonstrated. Differences in the stage progression-free rates were assessed by the log rank test, the Cochran-Mantel-Haenszel test, by setting significant level at a two-tailed P-value of <0.05.

No difference that would affect the results of analysis was observed in baseline characteristics between the BPS therapy group and the No BPS therapy group. Concerning the BPS therapy group, the 3-year stage progression-free rate (%) was 74.7, the standard error thereof was 12.9, and the 95% confidence interval was 49.4 to 99.9. Concerning the No BPS therapy group, in contrast, the 3-year stage progression-free rate (%) was 89.6, the standard error thereof was 2.9, and the 95% confidence interval was 83.9 to 95.4. The 3-year stage progression-free rate (%) of the BPS therapy group was 0.83 times that of the No BPS therapy group. The results of Kaplan-Meier analysis demonstrated that the average period (months) before progression into stage 4 of the BPS therapy group was 38.0, the standard error thereof was 2.1, and the 95% confidence interval was 33.9 to 42.1. In contrast, the results demonstrated that the average period (months) before progression into stage 4 of the No BPS therapy group was 40.9, the standard error thereof was 0.5, and the 95% confidence interval was 39.9 to 42.0. The average stage progression-free period of the BPS therapy group was 0.93 times that of the No BPS therapy group. A P value indicating a difference in the stage progression-free rate between the groups was 0.3159. That is, no effects of BPS administration to inhibit progression into stage 4 were observed in cats with CKD that had exhibited serum creatinine of 1.6 mg/dL to 2.8 mg/dL (stage 2) before initiation of administration (FIG. 4).

Example 3

As in the studies described in Example 2, the data sets of 218 cats diagnosed to have CKD exhibiting serum creatinine of 2.9 mg/dL to 5.0 mg/dL (stage 3) or higher than 5.0 mg/dL (stage 4) in accordance with the method defined by the IRIS staging were extracted, and the data sets of 199 cats exhibiting serum creatinine of 10.0 mg/dL or lower were analyzed. Based on the drug prescription records, cats were divided into two groups: a BPS therapy group consisting of 73 cats; and a BPS therapy-free group consisting of 126 cats.

In Example 3, the periods before kidney death were compared and analyzed retrospectively. The timing of kidney death was determined with reference to the guidelines on acute kidney insufficiency from the International Renal Interest Society. On the basis of the statement such that "a patient may die within 5 to 10 days despite appropriate conservative therapy without kidney replacement therapy if serum creatinine is higher than 10.0 mg/dL," specifically, kidney death was determined when serum creatinine of higher than 10.0 mg/dL was recorded in the serum creatinine test. By designating kidney death as the outcome, the start date of treatment as the point of origin for the cats in the BPS therapy group, and the start date of observation as the point of origin for the cats in the No BPS therapy group, the periods (months) before the outcome was observed were recorded. In analysis, the 3-year kidney survival rates (%) of the BPS therapy group and of the No BPS therapy group, the standard errors thereof, the 95% confidence intervals, and the comparison of the 3-year kidney survival rates (%) between the groups were calculated. The periods (months) before kidney death of the BPS therapy group and of the No BPS therapy group and the outcomes thereof were analyzed by Kaplan-Meier analysis to show curves demonstrating changes in the kidney survival rate relative to the observational period (months). As a case summary, kidney death, discontinuation, and the overall number were demonstrated. The average period (months) before kidney death, the standard error thereof, the 95% confidence interval, and the comparison of the average kidney survival periods were demonstrated. Differences in the kidney survival rates were assessed by the log rank test, the Cochran-Mantel-Haenszel test, by setting significant level at a two-tailed P-value of <0.05.

Figure 5:
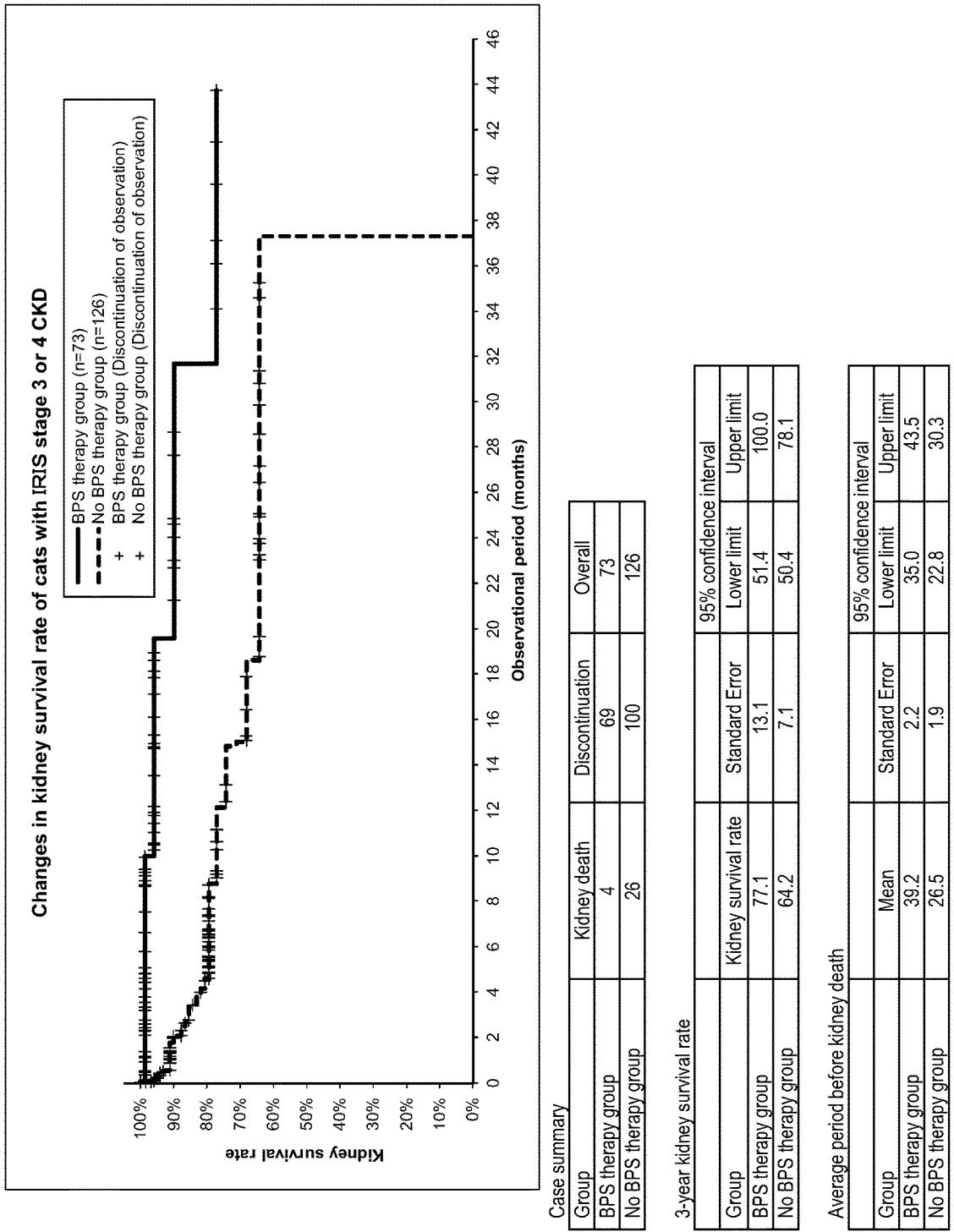
FIG. 5 is a view showing changes in kidney survival rates of cats having CKD with IRIS stage 3 or 4 in the BPS therapy group and in the No BPS therapy group.

Concerning the BPS therapy group, the 3-year kidney survival rate (%) was 77.1, the standard error thereof was 13.1, and the 95% confidence interval was 51.4 to 100.0. Concerning the No BPS therapy group, in contrast, the 3-year kidney survival rate (%) was 64.2, the standard error thereof was 7.1, and the 95% confidence interval was 50.4 to 78.1. The 3-year kidney survival rate (%) of the BPS therapy group was 1.20 times that of the No BPS therapy group. The results of Kaplan-Meier analysis demonstrated that the average period (months) before kidney death of the BPS therapy group was 39.2, the standard error thereof was 2.2, and the 95% confidence interval was 35.0 to 43.5. In contrast, the results demonstrated that the average period (months) before kidney death of the No BPS therapy group was 26.5, the standard error thereof was 1.9, and the 95% confidence interval was 22.8 to 30.3. The average kidney survival period of the BPS therapy group was 1.48 times that of the No BPS therapy group. A P value indicating a difference in the kidney survival rate between the groups was 0.0003. That is, effects of BPS administration to inhibit kidney death were observed in cats with CKD that had exhibited serum creatinine of 2.9 mg/dL to 5.0 mg/dL (stage 3) or higher than 5.0 mg/dL (stage 4) before initiation of administration (FIG. 5).

Comparative Example 2

As in the studies described in Comparative Example 1, as shown in FIG. 1, the data sets of 369 cats diagnosed to have CKD exhibiting serum creatinine of 1.6 mg/dL to 2.8 mg/dL (stage 2) in accordance with the method defined by the IRIS staging were extracted and analyzed. Based on the drug prescription records, cats were divided into two groups: a BPS therapy group consisting of 37 cats; and a BPS therapy-free group consisting of 332 cats.

In Comparative Example 2, the periods before kidney death were compared and analyzed retrospectively. The timing of kidney death was determined with reference to the guidelines on acute kidney insufficiency from the International Renal Interest Society. On the basis of the statement such that "a patient may die within 5 to 10 days despite appropriate conservative therapy without kidney replacement therapy if serum creatinine is higher than 10.0 mg/dL," specifically, kidney death was determined when serum creatinine of higher than 10.0 mg/dL was recorded in the serum creatinine test. By designating kidney death as the outcome, the start date of treatment as the point of origin for the cats in the BPS therapy group, and the start date of observation as the point of origin for the cats in the No BPS therapy group, the periods (months) before the outcome was observed were recorded. In analysis, the 3-year kidney survival rates (%) of the BPS therapy group and of the No BPS therapy group, the standard errors thereof, the 95% confidence intervals, and the comparison of the 3-year kidney survival rates (%) between the groups were calculated. The periods (months) before kidney death of the BPS therapy group and of the No BPS therapy group and the outcomes thereof were analyzed by Kaplan-Meier analysis to show curves demonstrating changes in the kidney survival rate relative to the observational period (months). As a case summary, kidney death, discontinuation, and the overall number were demonstrated. The average period (months) before kidney death, the standard error thereof, the 95% confidence interval, and the comparison of the average kidney survival periods were demonstrated. Differences in the kidney survival rates were assessed by the log rank test, the Cochran-Mantel-Haenszel test, by setting significant level at a two-tailed P-value of <0.05.

Concerning the BPS therapy group, the 3-year kidney survival rate (%) was 90.0, the standard error thereof was 9.5, and the 95% confidence interval was 71.4 to 100.0. Concerning the No BPS therapy group, in contrast, the 3-year kidney survival rate (%) was 95.2, the standard error thereof was 1.9, and the 95% confidence interval was 91.5 to 98.9. The 3-year kidney survival rate (%) of the BPS therapy group was 0.95 times that of the No BPS therapy group. The results of Kaplan-Meier analysis demonstrated that the average period (months) before kidney death of the BPS therapy group was 40.8, the standard error thereof was 1.3, and the 95% confidence interval was 38.3 to 43.3. In contrast, the results demonstrated that the average period (months) before kidney death of the No BPS therapy group was 41.9, the standard error thereof was 0.4, and the 95% confidence interval was 41.1 to 42.7. The average kidney survival period of the BPS therapy group was 0.97 times that of the No BPS therapy group. A P value indicating a difference in the kidney survival rate between the groups was 0.9049. That is, no effects of BPS administration to inhibit kidney death were observed in cats with CKD that had exhibited serum creatinine of 1.6 mg/dL to 2.8 mg/dL (stage 2) before initiation of administration (FIG. 6).

Example 4

As in the studies described in Example 2, the data sets of 134 cats diagnosed to have CKD exhibiting serum creatinine of 2.9 mg/dL to 5.0 mg/dL (stage 3) in accordance with the method of the IRIS staging were extracted and analyzed. Based on the drug prescription records, cats were divided into two groups: a BPS therapy group consisting of 57 cats; and a BPS therapy-free group consisting of 77 cats.

In Example 4, the survival periods were compared and analyzed retrospectively. By designating all-cause death as the outcome, the start date of treatment as the point of origin for the cats in the BPS therapy group, and the start date of observation as the point of origin for the cats in the No BPS therapy group based on the death records, the periods (months) before the outcome was observed were recorded. In analysis, the 3-year overall survival rates (%) of the BPS therapy group and of the No BPS therapy group, the standard errors thereof, the 95% confidence intervals, and the comparison of the 3-year overall survival rates (%) between the groups were calculated. The survival periods (months) of the BPS therapy group and the No BPS therapy group and the outcomes thereof were analyzed by Kaplan-Meier analysis to show survival curves demonstrating changes in the overall survival rate or the observed survival rate relative to the observational period (months). As a case summary, death, discontinuation, and the overall number were demonstrated. The average survival periods (months), the standard errors thereof, the 95% confidence intervals, the medians and the standard errors thereof, the 95% confidence intervals, and the comparison of the average survival periods were demonstrated. Differences in the overall survival rates were assessed by the log rank test, the Cochran-Mantel-Haenszel test, by setting significant level at a two-tailed P-value of <0.05.

Figure 7:
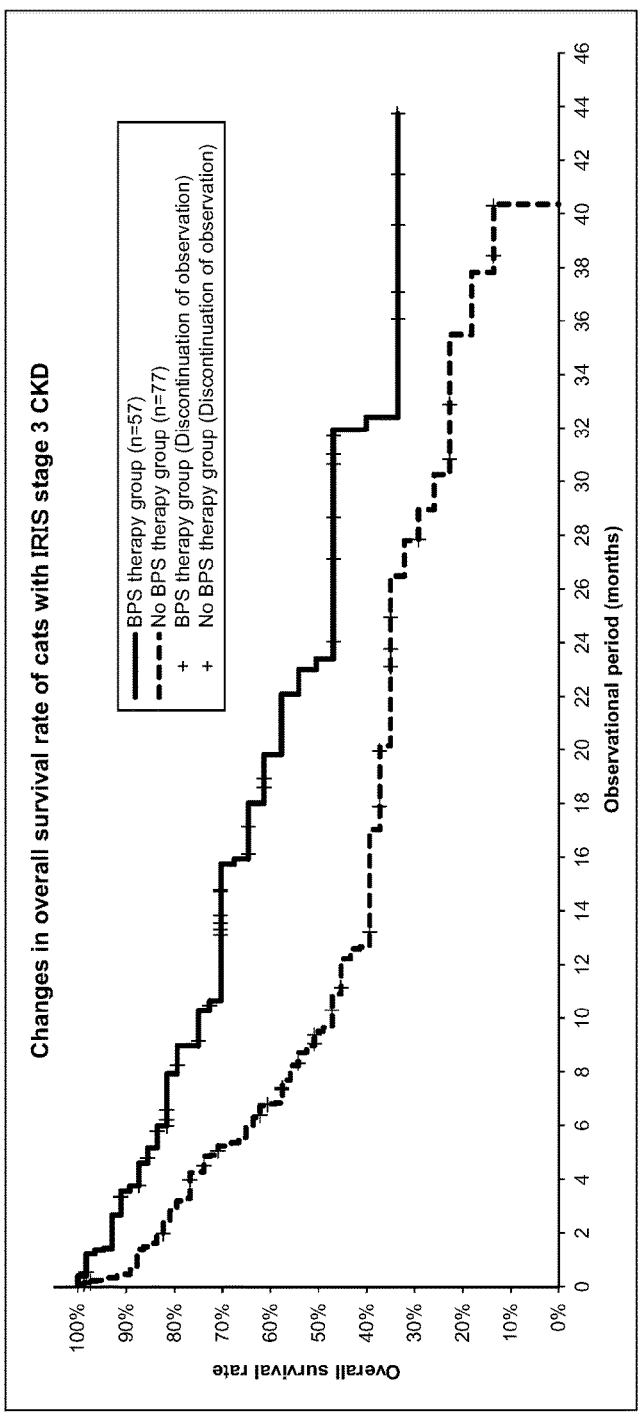
FIG. 7 is a view showing changes in overall survival rates of cats having CKD with IRIS stage 3 in the BPS therapy group and in the No BPS therapy group.

Concerning the BPS therapy group, the 3-year overall survival rate (%) was 33.5, the standard error thereof was 10.1, and the 95% confidence interval was 13.8 to 53.2. Concerning the No BPS therapy group, in contrast, the 3-year overall survival rate (%) was 18.1, the standard error thereof was 6.6, and the 95% confidence interval was 5.3 to 31.0. The 3-year overall survival rate (%) of the BPS therapy group was 1.85 times that of the No BPS therapy group. The results of Kaplan-Meier analysis demonstrated that the average survival period (months) of the BPS therapy group was 25.3, the standard error thereof was 2.5, the 95% confidence interval was 20.3 to 30.2, the median thereof was 23.4, the standard error thereof was 6.6, and the 95% confidence interval was 10.4 to 36.4. In contrast, the results demonstrated that the average survival period (months) of the No BPS therapy group was 16.4, the standard error thereof was 1.9, the 95% confidence interval was 12.6 to 20.1, the median thereof was 9.5, the standard error thereof was 2.3, and the 95% confidence interval was 5.1 to 13.9. The average survival period of the BPS therapy group was 1.54 times that of the No BPS therapy group. A P value indicating a difference in the overall survival rate between the groups was 0.0040. That is, effects of BPS administration to improve the overall survival rate or the observed survival rate were observed in cats with CKD that had exhibited serum creatinine of 2.9 mg/dL to 5.0 mg/dL (stage 3) before initiation of administration (FIG. 7).

Example 5

In the studies described in Example 2, as shown in FIG. 1, the data sets of 84 cats diagnosed to have CKD exhibiting serum creatinine of higher than 5.0 mg/dL (stage 4) in accordance with the method defined by the IRIS staging were extracted and analyzed.

Based on the drug prescription records, cats were divided into two groups: a BPS therapy group consisting of 17 cats; and a BPS therapy-free group consisting of 67 cats, and baseline characteristics and the survival periods were compared and analyzed retrospectively. To the cats in the BPS therapy group, BPS drugs for veterinary use, RAPROS (trademark) (Toray Industries, Inc.), were administered while adjusting the amount of BPS to 20.0 to 49.1 µg/kg body weight/day and the median to 31.4 µg/kg body weight/day twice daily during or after morning and evening feeding occasions. By designating all-cause death as the outcome, the start date of treatment as the point of origin for the cats in the BPS therapy group, and the start date of observation as the point of origin for the cats in the No BPS therapy group based on the death records, the periods (months) before the outcome was observed were recorded. In analysis, the 2-year overall survival rates (%) of the BPS therapy group and of the No BPS therapy group, the standard errors thereof, the 95% confidence intervals, and the comparison of the 2-year overall survival rates (%) between the groups were calculated. The survival periods (months) of the BPS therapy group and of the No BPS therapy group and the outcomes thereof were analyzed by Kaplan-Meier analysis to show survival curves demonstrating changes in the overall survival rate or the observed survival rate relative to the observational period (months). As a case summary, death, discontinuation, and the overall number were demonstrated. The average survival period (months), the standard error thereof, the 95% confidence interval, the median and the standard error thereof, the 95% confidence interval, and the comparison of the average survival periods were demonstrated. Differences in the overall survival rates were assessed by the log rank test, the Cochran-Mantel-Haenszel test, by setting significant level at a two-tailed P-value of <0.05.

Figure 8:
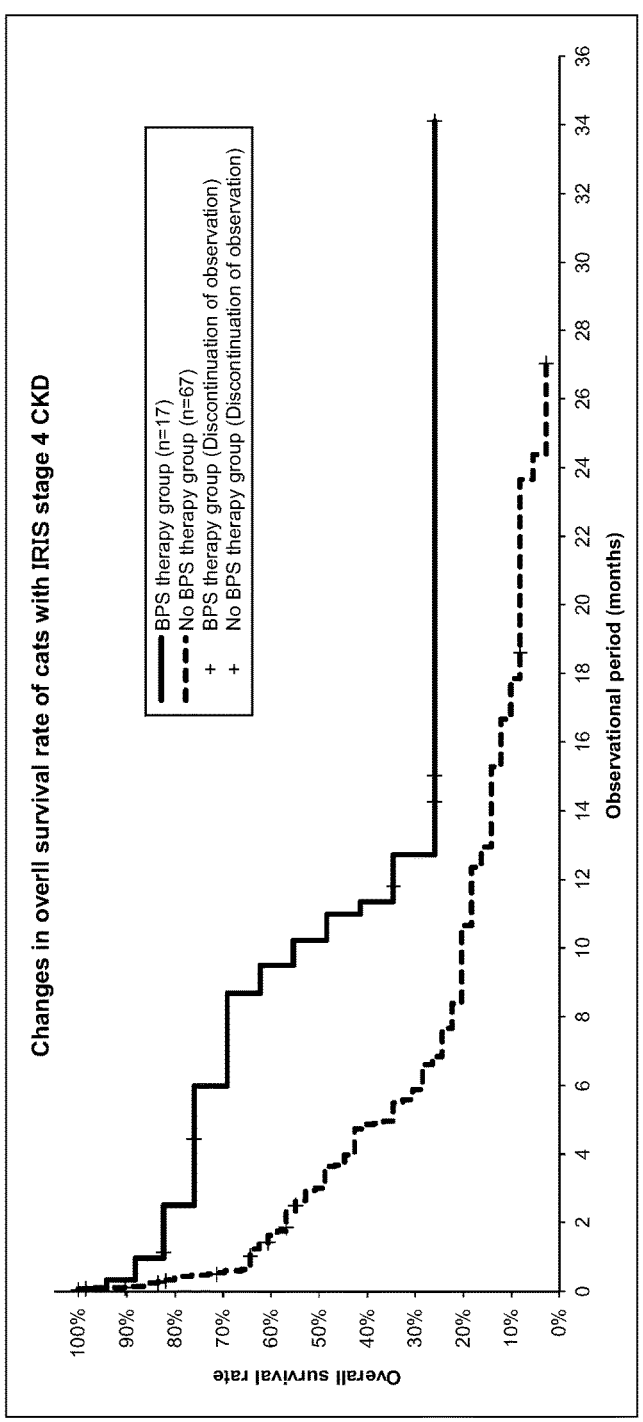
FIG. 8 is a view showing changes in overall survival rates of cats having CKD with IRIS stage 4 in the BPS therapy group and in the No BPS therapy group.

No difference that would affect the results of analysis was observed in baseline characteristics between the BPS therapy group and the No BPS therapy group. Concerning the BPS therapy group, the 2-year overall survival rate (%) was 25.9, the standard error thereof was 11.9, and the 95% confidence interval was 2.6 to 49.3. Concerning the No BPS therapy group, in contrast, the 2-year overall survival rate (%) was 5.4, the standard error thereof was 3.4, and the 95% confidence interval was 0 to 12.1. The 2-year overall survival rate (%) of the BPS therapy group was 4.80 times that of the No BPS therapy group. The results of Kaplan-Meier analysis demonstrated that the average survival period (months) of the BPS therapy group was 14.1, the standard error thereof was 3.3, the 95% confidence interval was 7.7 to 20.5, the median thereof was 10.2, the standard error thereof was 1.4, and the 95% confidence interval was 7.5 to 12.9. In contrast, the results demonstrated that the average survival period (months) of the No BPS therapy group was 5.8, the standard error thereof was 1.0, the 95% confidence interval was 3.8 to 7.8, the median thereof was 3.0, the standard error thereof was 1.1, and the 95% confidence interval was 0.9 to 5.1. The average survival period of the BPS therapy group was 2.43 times that of the No BPS therapy group. A P value indicating a difference in the overall survival rate between the groups was 0.0235. That is, effects of BPS administration to improve the overall survival rate or the observed survival rate were observed in cats with CKD that had exhibited serum creatinine of higher than 5.0 mg/dL (stage 4) before initiation of administration (FIG. 8).

Comparative Example 3

As in the studies described in Comparative Example 1, as shown in FIG. 1, the data sets of 369 cats diagnosed to have CKD exhibiting serum creatinine of 1.6 mg/dL to 2.8 mg/dL (stage 2) in accordance with the method defined by the IRIS staging were extracted and analyzed. Based on the drug prescription records, cats were divided into two groups: a BPS therapy group consisting of 37 cats; and a BPS therapy-free group consisting of 332 cats.

In Comparative Example 3, the survival periods were compared and analyzed retrospectively. By designating all-cause death as the outcome, the start date of treatment as the point of origin for the cats in the BPS therapy group, and the start date of observation as the point of origin for the cats in the No BPS therapy group based on the death records, the periods (months) before the outcome was observed were recorded. In analysis, the 3-year overall survival rates (%) of the BPS therapy group and of the No BPS therapy group, the standard errors thereof, the 95% confidence intervals, and the comparison of the 3-year overall survival rates (%) between the groups were calculated. The survival periods (months) of the BPS therapy group and of the No BPS therapy group and the outcomes thereof were analyzed by Kaplan-Meier analysis. On the basis thereof, death, discontinuation, and the overall number were demonstrated as a summary of cases. The average survival period (months), the standard error thereof, the 95% confidence interval, the median and the standard error thereof, the 95% confidence interval, and the comparison of the average survival periods were demonstrated. Differences in the overall survival rates were assessed by the log rank test, the Cochran-Mantel-Haenszel test, by setting significant level at a two-tailed P-value of <0.05.

Concerning the BPS therapy group, the 3-year overall survival rate (%) was 52.2, the standard error thereof was 11.8, and the 95% confidence interval was 29.1 to 75.3. Concerning the No BPS therapy group, in contrast, the 3-year overall survival rate (%) was 72.4, the standard error thereof was 3.3, and the 95% confidence interval was 65.8 to 78.9. The 3-year overall survival rate (%) of the BPS therapy group was 0.72 times that of the No BPS therapy group. The results of Kaplan-Meier analysis demonstrated that the average survival period (months) of the BPS therapy group was 31.5, the standard error thereof was 2.6, and the 95% confidence interval was 26.3 to 36.7. In contrast, the results demonstrated that the average survival period (months) of the No BPS therapy group was 35.1, the standard error thereof was 0.9, and the 95% confidence interval was 33.4 to 36.9. The average survival period of the BPS therapy group was 0.90 times that of the No BPS therapy group. A P value indicating a difference in the overall survival rate between the groups was 0.2637. That is, no effects of BPS administration to improve the overall survival rate or the observed survival rate were observed in cats with CKD that had exhibited serum creatinine of 1.6 mg/dL to 2.8 mg/dL (stage 2) before initiation of administration (FIG. 9).

Example 6

As the indicator of cats with CKD exhibiting body weight loss, "body weight of less than 4.2 kg" that is demonstrated to worsen life prognosis in L. M. Freeman et al. was used. As in the studies described in Example 2, the data sets of 134 cats diagnosed to have CKD exhibiting serum creatinine of 2.9 mg/dL to 5.0 mg/dL (stage 3) in accordance with the method defined by the IRIS staging were extracted, and the data sets of 89 cats having body weight of less than 4.2 kg were extracted and analyzed. Based on the drug prescription records, cats were divided into two groups: a BPS therapy group consisting of 35 cats; and a BPS therapy-free group consisting of 54 cats.

In Example 6, the survival periods were compared and analyzed retrospectively. By designating all-cause death as the outcome, the start date of treatment as the point of origin for the cats in the BPS therapy group, and the start date of observation as the point of origin for the cats in the No BPS therapy group based on the death records, the periods (months) before the outcome was observed were recorded. The 3-year overall survival rates (%) of the BPS therapy group and of the No BPS therapy group, the standard errors thereof, the 95% confidence intervals, and the comparison of the 3-year overall survival rates (%) between the groups were calculated. The survival periods (months) of the BPS therapy group and of the No BPS therapy group and the outcomes thereof were analyzed by Kaplan-Meier analysis to show survival curves demonstrating changes in the overall survival rate or the observed survival rate relative to the observational period (months). As a case summary, death, discontinuation, and the overall number were demonstrated. The average survival period (months), the standard error thereof, the 95% confidence interval, the median and the standard error thereof, the 95% confidence interval, and the comparison of the average survival periods were demonstrated. Differences in the overall survival rates were assessed by the log rank test, the Cochran-Mantel-Haenszel test, by setting significant level at a two-tailed P-value of <0.05.

Concerning the BPS therapy group, the 3-year overall survival rate (%) was 28.0, the standard error thereof was 11.1, and the 95% confidence interval was 6.2 to 49.8. Concerning the No BPS therapy group, in contrast, the 3-year overall survival rate (%) was 10.1, the standard error thereof was 5.9, and the 95% confidence interval was 0 to 21.7. The 3-year overall survival rate (%) of the BPS therapy group was 2.77 times that of the No BPS therapy group. The results of Kaplan-Meier analysis demonstrated that the average survival period (months) of the BPS therapy group was 22.4, the standard error thereof was 3.1, and the 95% confidence interval was 16.3 to 28.5, the median thereof was 19.8, the standard error thereof was 4.6, and the 95% confidence interval was 10.7 to 28.9. In contrast, the results demonstrated that the average survival period (months) of the No BPS therapy group was 14.5, the standard error thereof was 2.0, the 95% confidence interval was 10.5 to 18.4, the median thereof was 9.0, the standard error thereof was 1.5, and the 95% confidence interval was 6.1 to 11.9. The average survival period of the BPS therapy group was 1.54 times that of the No BPS therapy group. A P value indicating a difference in the overall survival rate between the groups was 0.0257. That is, effects of BPS administration to improve the overall survival rate or the observed survival rate were observed in cats with CKD that had exhibited serum creatinine of 2.9 mg/dL to 5.0 mg/dL (stage 3) and body weight of less than 4.2 kg before initiation of administration (FIG. 10). In Example 4, the 3-year overall survival rate (%) of the BPS therapy group was 1.85 times that of the No BPS therapy group. In Example 6, in contrast, the 3-year overall survival rate (%) of the BPS therapy group was 2.77 times that of the No BPS therapy group. That is, remarkable efficacy of our agent was exerted on cats with CKD exhibiting body weight loss to less than 4.2 kg.

From among the cats with CKD, the data sets of 69 cats having body weight of less than 3.5 kg were extracted, and the cats were divided into two groups: a BPS therapy group consisting of 19 cats; and a BPS therapy-free group consisting of 40 cats. In the same manner as described above, the 3-year overall survival rates (%) and the average survival periods were compared between the groups. The results of comparison demonstrate that the 3-year overall survival rate (%) of the BPS therapy group was 2.90 times that of the No BPS therapy group, and the average survival period of the BPS therapy group was 1.66 times that of the No BPS therapy group. That is, remarkable efficacy of our agent was further demonstrated.

The invention claimed is:
1. A therapeutic method for a cat with chronic kidney disease to inhibit kidney death of a cat with chronic kidney disease by administering a therapeutic agent comprising, as an active ingredient, a compound represented by the formula (I) to a cat with stage 4 chronic kidney disease defined by the staging system established by the International Renal Interest Society (the IRIS staging) in an amount of 90 to 130 μg of the compound represented by the formula (I) daily:

[Formula 1]

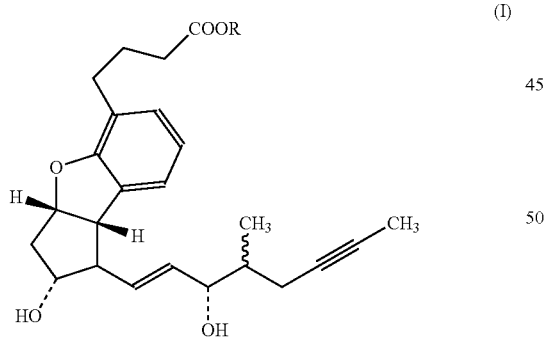

(I)

wherein R represents hydrogen or a pharmacologically acceptable cation.

2. A therapeutic method for a cat with chronic kidney disease to improve the overall survival rate or the observed survival rate of a cat with chronic kidney disease by administering a therapeutic agent comprising, as an active ingredient, a compound represented by the formula (I) to a cat with stage 4 chronic kidney disease defined by the staging system established by the International Renal Interest Society (the IRIS staging) in an amount of 90 to 130 μg of the compound represented by the formula (I) daily:

[Formula 2]

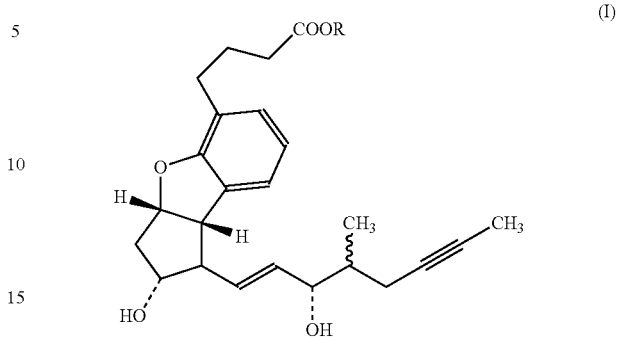

(I)

wherein R represents hydrogen or a pharmacologically acceptable cation.

3. A therapeutic method for a cat with chronic kidney disease to improve the overall survival rate or the observed survival rate of a cat with chronic kidney disease by administering a therapeutic agent comprising, as an active ingredient, a compound represented by the formula (I) to a cat with stage 3 chronic kidney disease defined by the staging system established by the International Renal Interest Society (the IRIS staging) in an amount of 90 to 130 μg of the compound represented by the formula (I) daily:

[Formula 3]

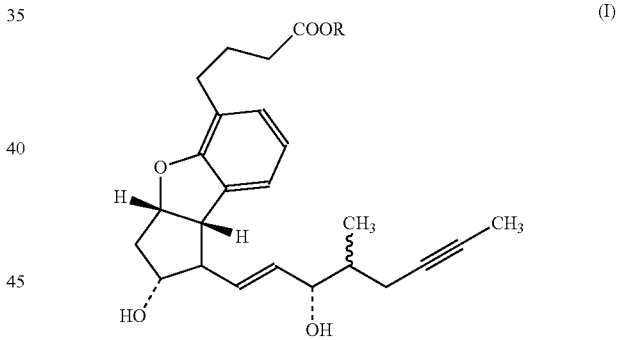

(I)

wherein R represents hydrogen or a pharmacologically acceptable cation.

4. A therapeutic method for a cat with chronic kidney disease to improve the overall survival rate or the observed survival rate of a cat with chronic kidney disease by administering a therapeutic agent comprising, as an active ingredient, a compound represented by the formula (I) to a cat with stage 3 chronic kidney disease defined by the staging system established by the International Renal Interest Society (the IRIS staging) having also complications/comorbidities selected from chronic heart failure, diabetes mellitus, pancreatitis, neoplasia, hyperthyroidism, hypertension, proteinuria, hypokalemia, hyperphosphatemia, or anemia in an amount of 90 to 130 μg of the compound represented by the formula (I) daily:

[Formula 4]

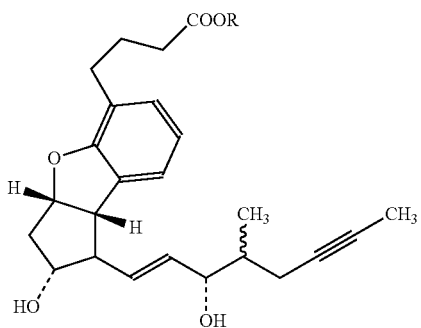

(I)

wherein R represents hydrogen or a pharmacologically acceptable cation.

5. A therapeutic method for a cat with chronic kidney disease to improve the overall survival rate or the observed survival rate of a cat with chronic kidney disease by administering a therapeutic agent comprising, as an active ingredient, a compound represented by the formula (I) to a cat with stage 3 or 4 chronic kidney disease defined by the staging system established by the International Renal Interest Society (the IRIS staging) exhibiting body weight loss to less than 4.2 kg in an amount of 90 to 130 μg of the compound represented by the formula (I) daily:

[Formula 5]

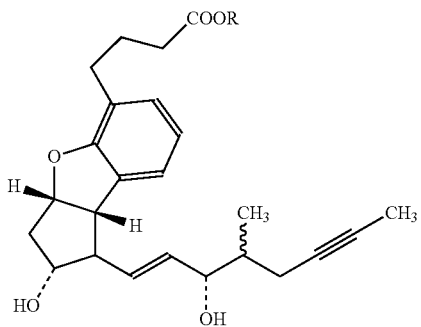

(I)

wherein R represents hydrogen or a pharmacologically acceptable cation.

6. The therapeutic method according to claim 1, wherein the compound represented by the formula (I) is beraprost sodium.

7. The therapeutic method according to claim 2, wherein the compound represented by the formula (I) is beraprost sodium.

8. The therapeutic method according to claim 3, wherein the compound represented by the formula (I) is beraprost sodium.

9. The therapeutic method according to claim 4, wherein the compound represented by the formula (I) is beraprost sodium.

10. The therapeutic method according to claim 5, wherein the compound represented by the formula (I) is beraprost sodium.

11. The therapeutic method according to claim 1, wherein the cat having chronic kidney disease with IRIS stage 4 exhibits body weight loss to less than 4.2 kg.

12. The therapeutic method according to claim 2, wherein the cat having chronic kidney disease with IRIS stage 4 exhibits body weight loss to less than 4.2 kg.

13. The therapeutic method according to claim 3, wherein the cat having chronic kidney disease with IRIS stage 3 exhibits body weight loss to less than 4.2 kg.

14. The therapeutic method according to claim 4, wherein the cat having chronic kidney disease with IRIS stage 3 exhibits body weight loss to less than 4.2 kg.

15. The therapeutic method according to claim 3, wherein the cat having chronic kidney disease with IRIS stage 3 exhibits serum creatinine of 2.9 mg/dL to 5.0 mg/dL and serum SDMA of 9.0 μg/dL or higher.

16. The therapeutic method according to claim 4, wherein the cat having chronic kidney disease with IRIS stage 3 exhibits serum creatinine of 2.9 mg/dL to 5.0 mg/dL and serum SDMA of 9.0 μg/dL or higher.

17. The therapeutic method according to claim 5, wherein the cat having chronic kidney disease with IRIS stage 3 exhibits serum creatinine of 2.9 mg/dl to 5.0 mg/dL and serum SDMA of 9.0 μg/dL or higher.

18. The therapeutic method according to claim 1, wherein the cat having chronic kidney disease with IRIS stage 4 exhibits serum creatinine of higher than 5.0 mg/dl and serum SDMA of 9.0 μg/dL or higher.

19. The therapeutic method according to claim 2, wherein the cat having chronic kidney disease with IRIS stage 4 exhibits serum creatinine of higher than 5.0 mg/dL and serum SDMA of 9.0 μg/dL or higher.

20. The therapeutic method according to claim 5, wherein the cat having chronic kidney disease with IRIS stage 4 exhibits serum creatinine of higher than 5.0 mg/dL and serum SDMA of 9.0 μg/dL or higher.

21. The therapeutic method according to claim 5, wherein the therapeutic agent is administered to the cat having chronic kidney disease with IRIS stage 3.

22. The therapeutic method according to claim 1, wherein the cat having chronic kidney disease with IRIS stage 4 satisfies the serum creatinine criterion of the IRIS staging criteria.

23. The therapeutic method according to claim 2, wherein the cat having chronic kidney disease with IRIS stage 4 satisfies the serum creatinine criterion of the IRIS staging criteria.

24. The therapeutic method according to claim 3, wherein the cat having chronic kidney disease with IRIS stage 3 satisfies the serum creatinine criterion of the IRIS staging criteria.

25. The therapeutic method according to claim 4, wherein the cat having chronic kidney disease with IRIS stage 3 satisfies the serum creatinine criterion of the IRIS staging criteria.

26. The therapeutic method according to claim 5, wherein the cat having chronic kidney disease with IRIS stage 3 or 4 satisfies the serum creatinine criterion of the IRIS staging criteria.

27. The therapeutic method according to claim 1, wherein the compound represented by the formula (I) is administered to the cat with chronic kidney disease in an amount of 14.1 to 52.4 μg/kg body weight/day.

28. The therapeutic method according to claim 2, wherein the compound represented by the formula (I) is administered to the cat with chronic kidney disease in an amount of 14.1 to 52.4 μg/kg body weight/day.

29. The therapeutic method according to claim 3, wherein the compound represented by the formula (I) is administered 30. The therapeutic method according to claim 4, wherein the compound represented by the formula (I) is administered to the cat with chronic kidney disease in an amount of 14.1 to 52.4 μg/kg body weight/day.

31. The therapeutic method according to claim 5, wherein the compound represented by the formula (I) is administered to the cat with chronic kidney disease in an amount of 14.1 to 52.4 μg/kg body weight/day.

32. The therapeutic method according to claim 1, wherein administration to the cat with chronic kidney disease is performed twice daily.

33. The therapeutic method according to claim 2, wherein administration to the cat with chronic kidney disease is performed twice daily.

34. The therapeutic method according to claim 3, wherein administration to the cat with chronic kidney disease is performed twice daily.

35. The therapeutic method according to claim 4, wherein administration to the cat with chronic kidney disease is performed twice daily.

36. The therapeutic method according to claim 5, wherein administration to the cat with chronic kidney disease is performed twice daily.

37. The therapeutic method according to claim 1, wherein administration to the cat with chronic kidney disease is performed during or after feeding.

38. The therapeutic method according to claim 2, wherein administration to the cat with chronic kidney disease is performed during or after feeding.

39. The therapeutic method according to claim 3, wherein administration to the cat with chronic kidney disease is performed during or after feeding.

40. The therapeutic method according to claim 4, wherein administration to the cat with chronic kidney disease is performed during or after feeding.

41. The therapeutic method according to claim 5, wherein administration to the cat with chronic kidney disease is performed during or after feeding.

42. The therapeutic method according to claim 1, wherein administration to the cat with chronic kidney disease is performed in addition to a standard care for feline chronic kidney disease.

43. The therapeutic method according to claim 2, wherein administration to the cat with chronic kidney disease is performed in addition to a standard care for feline chronic kidney disease.

44. The therapeutic method according to claim 3, wherein administration to the cat with chronic kidney disease is performed in addition to a standard care for feline chronic kidney disease.

45. The therapeutic method according to claim 4, wherein administration to the cat with chronic kidney disease is performed in addition to a standard care for feline chronic kidney disease.

46. The therapeutic method according to claim 5, wherein administration to the cat with chronic kidney disease is performed in addition to a standard care for feline chronic kidney disease.

47. The therapeutic method according to claim 42, wherein the standard care is a therapeutic method defined by the guidelines from the International Society of Feline Medicine or the International Renal Interest Society.

48. The therapeutic method according to claim 43, wherein the standard care is a therapeutic method defined by the guidelines from the International Society of Feline Medicine or the International Renal Interest Society.

49. The therapeutic method according to claim 44, wherein the standard care is a therapeutic method defined by the guidelines from the International Society of Feline Medicine or the International Renal Interest Society.

50. The therapeutic method according to claim 45, wherein the standard care is a therapeutic method defined by the guidelines from the International Society of Feline Medicine or the International Renal Interest Society.

51. The therapeutic method according to claim 46, wherein the standard care is a therapeutic method defined by the guidelines from the International Society of Feline Medicine or the International Renal Interest Society.

52. The therapeutic method according to claim 1, wherein the cat with chronic kidney disease also has chronic heart failure, diabetes mellitus, pancreatitis, neoplasia, hyperthyroidism, hypertension, proteinuria, hypokalemia, hyperphosphatemia, or anemia.

53. The therapeutic method according to claim 2, wherein the cat with chronic kidney disease also has chronic heart failure, diabetes mellitus, pancreatitis, neoplasia, hyperthyroidism, hypertension, proteinuria, hypokalemia, hyperphosphatemia, or anemia.

54. The therapeutic method according to claim 3, wherein the cat with chronic kidney disease also has chronic heart failure, diabetes mellitus, pancreatitis, neoplasia, hyperthyroidism, hypertension, proteinuria, hypokalemia, hyperphosphatemia, or anemia.

55. The therapeutic method according to claim 5, wherein the cat with chronic kidney disease also has chronic heart failure, diabetes mellitus, pancreatitis, neoplasia, hyperthyroidism, hypertension, proteinuria, hypokalemia, hyperphosphatemia, or anemia.

* * * * *